US010577188B2

(12) United States Patent
Dent et al.

(10) Patent No.: US 10,577,188 B2
(45) Date of Patent: *Mar. 3, 2020

(54) APPARATUS AND METHODS FOR DISPENSING PRE-FILLED CONTAINERS WITH PRECISELY-APPLIED PATIENT-SPECIFIC INFORMATION

(71) Applicant: ARxIUM, Inc., Buffalo Grove, IL (US)

(72) Inventors: Jacob A. Dent, Wildwood, IL (US); Brian Gorman, Lake Toxaway, NC (US); Mark Bidus, Prospect Heights, IL (US)

(73) Assignee: ARxIUM, Inc., Buffalo Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/209,368

(22) Filed: Dec. 4, 2018

(65) Prior Publication Data

US 2019/0100384 A1 Apr. 4, 2019

Related U.S. Application Data

(63) Continuation of application No. 15/845,731, filed on Dec. 18, 2017, now Pat. No. 10,173,845, which is a (Continued)

(51) Int. Cl.
*B32B 41/00* (2006.01)
*B65G 43/08* (2006.01)
(Continued)

(52) U.S. Cl.
CPC ............ *B65G 43/08* (2013.01); *G06F 19/00* (2013.01); *G06F 19/3462* (2013.01);
(Continued)

(58) Field of Classification Search
CPC ....... B65G 43/08; G09F 3/0288; H04L 67/12; G07F 11/42; G07F 11/62; G07F 17/0092;
(Continued)

(56) References Cited

U.S. PATENT DOCUMENTS 4,519,522 A 5/1985 McElwee
5,058,724 A 10/1991 Hinton
(Continued)

FOREIGN PATENT DOCUMENTS

CA 2520399 10/2004
WO WO 2004/036479 4/2004

OTHER PUBLICATIONS

U.S. Food and Drug Administration, National Drug Code Directory, http://www.fda.gov/drugs/informationdrugs/ucm142438.htm.
(Continued)

*Primary Examiner* — Michael N Orlando
*Assistant Examiner* — Joshel Rivera
(74) *Attorney, Agent, or Firm* — Reinhart Boerner Van Deuren s.c.

(57) ABSTRACT

Apparatus and methods for fulfillment of patient prescription orders by adapting a standard or stock container pre-filled with medication or the like for use as a patient-specific container through precise application of patient-specific information to the pre-filled container. Precise placement of the patient-specific information to the pre-filled container enables pharmacy management to fully utilize valuable information provided with the pre-filled container, thereby improving the quality of service to the patient while making the process of prescription order fulfillment more efficient. In general, preferred embodiments comprise control apparatus and information-application apparatus. In embodiments, the information-application apparatus is adapted to place a patient-specific label on the container. Preferred forms of the information-application apparatus include a label printer and a positioner. The preferred printer applies patient-specific information on a label. The preferred positioner orients the pre-filled container to receive the label (Continued)

from the printer such that information provided with the container is available for use.

20 Claims, 20 Drawing Sheets

Related U.S. Application Data continuation of application No. 14/619,913, filed on Feb. 11, 2015, now Pat. No. 9,878,853, which is a continuation of application No. 13/536,594, filed on Jun. 28, 2012, now Pat. No. 8,986,476, which is a continuation of application No. 11/142,979, filed on Jun. 2, 2005, now Pat. No. 8,231,749.

(51) Int. Cl.
| | |
|---|---|
| G09F 3/00 | (2006.01) |
| G06F 19/00 | (2018.01) |
| G06Q 50/24 | (2012.01) |
| G07F 11/16 | (2006.01) |
| G07F 11/42 | (2006.01) |
| G07F 11/62 | (2006.01) |
| G07F 17/00 | (2006.01) |
| H04L 29/08 | (2006.01) |
| G16H 10/60 | (2018.01) |
| G16H 20/13 | (2018.01) |
| G16H 20/10 | (2018.01) |
| A61J 7/00 | (2006.01) |

(52) U.S. Cl.
CPC .......... *G06Q 50/24* (2013.01); *G07F 11/165* (2013.01); *G07F 11/42* (2013.01); *G07F 11/62* (2013.01); *G07F 17/0092* (2013.01); *G09F 3/0288* (2013.01); *G16H 10/60* (2018.01); *G16H 20/10* (2018.01); *G16H 20/13* (2018.01); *H04L 67/12* (2013.01); *A61J 7/0084* (2013.01); *A61J 2205/10* (2013.01); *A61J 2205/30* (2013.01); *A61J 2205/60* (2013.01); *Y04S 40/18* (2018.05); *Y10T 156/1062* (2015.01); *Y10T 156/12* (2015.01); *Y10T 156/17* (2015.01); *Y10T 156/1702* (2015.01); *Y10T 156/1734* (2015.01); *Y10T 156/1744* (2015.01); *Y10T 156/1768* (2015.01)

(58) Field of Classification Search
CPC ... G07F 11/165; G06F 19/3462; G06Q 50/24; Y10T 156/1744; Y10T 156/1768; Y10T 156/12; Y10T 156/1702; Y10T 156/1734; Y10T 156/17; Y10T 156/1062; A61J 2205/60; A61J 2205/10; A61J 2205/30; A61J 7/0084
USPC ......... 156/64, 235, 256, 360, 378, 379, 510, 156/538, 539, 552, 556, 566, DIG. 2, 156/DIG. 25, DIG. 27, DIG. 44, DIG. 45, 156/DIG. 47
See application file for complete search history.

(56) References Cited

U.S. PATENT DOCUMENTS

| | | |
|---|---|---|
| 5,597,995 A | 1/1997 | Williams et al. |
| 5,713,485 A | 2/1998 | Liff et al. |
| 5,771,657 A | 6/1998 | Lasher et al. |
| 5,797,515 A | 8/1998 | Liff et al. |
| 5,798,020 A | 8/1998 | Coughlin et al. |
| 5,812,410 A | 9/1998 | Lion et al. |
| 5,838,575 A | 11/1998 | Lion |
| 5,963,453 A | 10/1999 | East |
| 5,964,374 A | 10/1999 | Yuyama et al. |
| 5,971,594 A | 10/1999 | Sahai et al. |
| 6,068,156 A | 5/2000 | Liff et al. |
| 6,152,364 A | 11/2000 | Schoonen et al. |
| 6,283,322 B1 | 9/2001 | Liff et al. |
| 6,352,200 B1 | 3/2002 | Schoonen et al. |
| 6,428,640 B1 | 8/2002 | Stevens et al. |
| 6,464,142 B1 | 10/2002 | Denenberg et al. |
| 6,471,089 B2 | 10/2002 | Liff et al. |
| 6,490,502 B2 | 12/2002 | Fellows et al. |
| 6,529,801 B1 | 3/2003 | Rosenblum |
| 6,564,121 B1 | 5/2003 | Wallace et al. |
| 6,581,798 B2 | 6/2003 | Liff et al. |
| 6,697,704 B2 | 2/2004 | Rosenblum |
| 6,735,497 B2 | 5/2004 | Wallace et al. |
| 6,766,218 B2 | 7/2004 | Rosenblum |
| 6,776,304 B2 | 8/2004 | Liff et al. |
| 6,814,254 B2 | 11/2004 | Liff et al. |
| 6,814,255 B2 | 11/2004 | Liff et al. |
| 6,874,684 B1 | 4/2005 | Denenberg et al. |
| 6,892,941 B2 | 5/2005 | Rosenblum |
| 7,080,755 B2 | 7/2006 | Handfield et al. |
| 7,242,301 B2 | 7/2007 | August et al. |
| 7,672,859 B1 | 3/2010 | Louie et al. |
| 7,865,398 B2 | 1/2011 | Schon |
| 8,231,749 B2 | 7/2012 | Dent et al. |
| 8,986,476 B2 | 3/2015 | Dent et al. |
| 9,878,853 B2 | 1/2018 | Dent et al. |
| 10,173,845 B2 * | 1/2019 | Dent .................... G06Q 50/24 |
| 2001/0002448 A1 | 5/2001 | Wilson et al. |
| 2002/0185212 A1 | 12/2002 | Schaupp et al. |
| 2003/0074218 A1 | 4/2003 | Liff et al. |
| 2003/0088333 A1 | 5/2003 | Liff et al. |
| 2003/0216831 A1 | 11/2003 | Hart et al. |
| 2004/0164146 A1 | 8/2004 | Rosenblum |
| 2005/0065645 A1 | 3/2005 | Liff et al. |
| 2005/0098626 A1 | 5/2005 | Jordan et al. |
| 2005/0230478 A1 | 10/2005 | Chapman et al. |
| 2007/0102109 A1 | 5/2007 | Katritzky et al. |
| 2012/0267032 A1 | 10/2012 | Dent et al. |

OTHER PUBLICATIONS

System Solutions for Automated Product Handling. Digital Video Disc including brochures and five video files. Source: Rowa Automatisierungssysteme GmbH & Co. KG., Kelborn, Germany. Date: Portions Copyrighted.
System Solutions for Automated Product Handling. Index Page from DVD. Source: Rowa Automatisierungssysteme GmbH & Co. KG., Kelborn, Germany. Date: Unknown. (2 pages).
System Solutions for Automated Product Handling. Rowa Information Pages from DVD. Source: Rowa Automatisierungssysteme GmbH & Co. KG. Date: Unknown. (1 page).
System Solutions for Automated Product Handling. Rowa-Options Information Pages from DVD. Source: Rowa Automatisierungssysteme GmbH & Co. KG. Date: Unknown. (1 page).
System Solutions for Automated Product Handling. Rowa brochure from DVD. Source: Rowa Automatisierungssysteme GmbH & Co. KG. Date: Unknown (8 pages).
System Solutions forAutomated Product Handling. Rowa Visavia brochure from DVD. Source: Rowa Automatisierungssysteme GmbH & Co. KG. Date: Unknown (1 page).
System Solutions for Automated Product Handling. Rowa Technical Data from DVD. Source: Rowa Automatisierungssysteme GmbH & Co. KG. Date: Jul. 2005 (2 pages).
ARX Ltd. Internet Site Excerpts. www.arxintern.net. Source: ARX, Ltd., United Kingdom. Date: Unknown. (7 pages).
Pharmacy Automation System: Rowa Speedcase System in U- and L-Configuration, with Ward Box Picking Software and PRIMA Automatic Labeler. Source: www.ids-healthcare.com. Date: Unknown. (4 pages).

* cited by examiner

APPARATUS AND METHODS FOR DISPENSING PRE-FILLED CONTAINERS WITH PRECISELY-APPLIED PATIENT-SPECIFIC INFORMATION

CROSS-REFERENCE TO RELATED PATENT APPLICATIONS

This application is a continuation of U.S. application Ser. No. 15/845,731, filed Dec. 18, 2017, which is a continuation of U.S. application Ser. No. 14/619,913, filed Feb. 11, 2015, now U.S. Pat. No. 9,878,853, which is a continuation of U.S. application Ser. No. 13/536,594, filed Jun. 28, 2012, now U.S. Pat. No. 8,986,476, which is a continuation of U.S. application Ser. No. 11/142,979, filed Jun. 2, 2005, now U.S. Pat. No. 8,231,749, all of which are incorporated herein by reference in their entireties.

FIELD OF THE INVENTION

The field relates in general to the dispensing of medication and like products and, more specifically, to the application of patient-specific information to containers used to hold such medication and products.

BACKGROUND OF THE INVENTION

The efficient and accurate dispensing of medication and like products by a pharmacy is important to the process of fulfilling patient prescription orders. Fulfillment of a patient prescription order refers to the process of providing medication and other articles and things to a patient (or care giver acting for the patient) responsive to a prescription. The prescription order may be fulfilled by any suitable pharmacy including, for example, retail pharmacies, mail order outpatient pharmacies, and hospital/extended care inpatient pharmacies.

A prescription order fulfilled by such pharmacies will typically comprise one or more prescriptions for medication and may include other articles and things, such as nutriceuticals (e.g, nutritional supplements and vitamins), over-the-counter ("OTC") medications, therapeutics, medication applicators, bandages, tape and like items. It is of the utmost importance to fulfill each prescription order such that the patient is provided with the correct medication, products, articles and things of the highest quality and to do so in a way which is as cost-effective as possible.

One way of fulfilling patient prescription orders for medication and like items has been to provide medication in a pre-filled container, such as a bottle, vial or other container type. The pre-filled containers are typically loaded by the manufacturer, repackager or other supplier. The pre-filled containers are delivered to the pharmacy responsible for fulfillment of the patient prescription orders whereupon they are kept in stock or inventory without special modification of the pre-filled containers. The pre-filled containers are a stock item.

The pre-filled containers are provided in various volumetric sizes, such as 75, 120 and 200 cubic centimeter containers. The pre-filled containers are typically loaded with a specific quantity of one or more medications or the like. The medications and like products may be in any suitable form such as tablets, powders or liquids.

After loading, a removable safety seal, such as a film or foil seal, may be applied across the container opening. A cap or other closure is then applied across the container opening. The closure can be any suitable type, such as a screw-on cap or a snap-fit cap. The closure is typically child-resistant and is replaceable over the opening, permitting the pre-filled container to be repeatably opened and closed to remove the medication. A tamper-evident neck seal may be applied to the cap.

The pre-filled containers are removed from inventory at the pharmacy when needed to fulfill a patient prescription order. Typically, a label including patient-specific information as required by the prescription order is applied to the container. Depending on the resources of the pharmacy, the pre-filled containers may be removed from inventory by means of an automatic product dispenser or may be selected from inventory by a pharmacy worker who might retrieve the desired pre-filled container from a pharmacy storage location. Labels containing the patient-specific information may be applied by an automatic labeler or applied by hand.

There are many advantages to using pre-filled containers for fulfillment of patient prescription orders. One very important advantage is that the pre-filled containers are provided with detailed information, or indicia, which fully identifies the medication held in the pre-filled container. Such information is of critical value to pharmacy management, physicians, health care workers and, above all, the patient. The information permits proper and efficient handling of the pre-filled container throughout the entire distribution process, from point of manufacture (or repackaging) to delivery to the patient.

Information provided on the pre-filled containers may include the manufacturer or supplier name, medication type, medication strength and description, lot number, expiration date and a National Drug Code ("NDC") identification symbol. Other important information may be provided such as drug interaction notices and a photograph, text or other representation or description of the appearance of the medication or product in the container. Information on the pre-filled containers is regulated by pharmacy and/or Food and Drug Administration regulations. As regulations change over time, the information on the pre-filled containers will change to comply with the new regulations.

The information provided on or with the pre-filled containers is typically in the form of both human-readable and machine-readable information. Bar codes consisting of spaced-apart light and dark elements are one example of a form of machine-readable information which may be provided on the pre-filled containers. Radio Frequency Identification ("RFD") tags are another type of machine-readable information which may be associated with pre-filled containers. The information provided on or with the pre-filled containers enables pharmacy management to immediately identify the medication contained in each pre-filled container and to easily manage an inventory of such pre-filled containers using commercially available inventory management tools.

Another advantage of pre-filled containers is that the use of such containers enables pharmacy management to provide better, less expensive service to the patient. For example, pharmacy management can provide better control over the quality, consistency and purity of the medication because the pre-filled container remains sealed from the point of manufacture or repackaging, up to and including delivery to the patient. And, errors associated with selecting an incorrect medication or miscounting medication are reduced or avoided completely because manual hand or machine counting of individual tablets is unnecessary.

Avoidance of manual hand or machine counting of tablets frees the pharmacist to consult with the patient, thereby providing a higher standard of care. By reducing the labor required to fulfill the order, pharmacy management is able to better control cost. And, use of pre-filled containers with clear markings and content descriptions provides an opportunity for improved control over valuable medication and product inventory.

However, there are disadvantages to existing methods of utilizing pre-filled containers in the prescription order fulfillment process. In order to convert one of many identical pre-filled containers for use as a patient-specific container for fulfillment of a patient prescription order, it is necessary to affix patient-specific information to the container. This is typically accomplished by affixing an adhesive-backed label to the pre-filled container. The labels are supplied on a release liner (such as wax paper or the like) and are removably affixed to the release liner. The information may be affixed to the label in any suitable manner, such as by printing with any commercially-available printer. The patient-specific information affixed to the label will include important information such as the patient name, medication type, medication strength and description, physician information, signa, instructions for taking the medication and one or more types of machine-readable information, such as a bar code.

Disadvantageously, the use of known label applicators or hand application of labels can result in indiscriminate application of the labels. Indiscriminate application of a label represents a problem to pharmacy management because some or all of the valuable information provided on the pre-filled containers may be covered and obscured by the label. As a result, the information provided with the pre-filled container may be rendered unusable to pharmacy management, patient or others in the prescription order fulfillment chain.

As an example, pharmacy management may wish to match the contents of the pre-filled container to the prescription order by utilizing both the manufacturer-applied bar code on the pre-filled container and the bar code printed on the patient-specific label. A match of the bar code information on the pre-filled container and on the label provides a powerful indication that the correct medication, at the correct strength, has been matched to the correct patient. However, if the bar code on the pre-filled container is covered by the label then this verification process is not possible.

By way of further example, pharmacy management may wish to read a lot number or expiration date of the labeled container following application of the patient-specific label. Or, a patient who has received a pre-filled container in fulfillment of her prescription order may wish to read a drug interaction notice or other element of information provided by the manufacturer or repackager. None of this is possible if the patient-specific label covers or obscures some or all of the information provided on the pre-filled container.

One approach to dispensing pre-filled containers is described in U.S. Patent Application Publication No. 2003/0216831. The system shown in the publication employs a laser to engrave information on a special label applied to the container. This approach, while quite effective for the intended use, requires that the containers be provided with a special label having a region for receiving the laser-engraved information. Containers as generally provided by the manufacturer, repackager or other supplier do not include such specialized labels.

It would be a significant advance in the art to provide an apparatus and method permitting pharmacy management to automatically convert non-patient-specific pre-filled containers from stock into use as patient-specific containers and to do so in a way which would permit pharmacy management to fully utilize and optimize the use of information provided on the pre-filled container by the manufacturer, repackager or other supplier.

SUMMARY

The subject matter described herein represents an improvement to the process of fulfilling patient prescription orders. A patient refers to any person seeking fulfillment of a prescription. More specifically, the subject matter described herein enables pharmacy management to automatically convert non-patient-specific pre-filled containers of medication, nutriceuticals, OTC medications, therapeutics and like products into patient-specific containers as required by the patient's prescription order.

These pre-filled containers are standard "stock" containers because the pre-filled containers are in a form as provided by the manufacturer, repackager or other supplier and utilized by the pharmacy without any requirement for modification of the pre-filled containers prior to conversion of each container to a patient-specific container. As can be readily appreciated, it is advantageous to utilize pre-filled stock containers because pharmacy management is not required to incur further costs associated with modification of the containers before adapting them for use as patient-specific containers.

Conversion of such pre-filled containers to patient-specific pre-filled containers is advantageously accomplished in a way which optimizes the use and value of information already provided on each pre-filled container, thereby providing pharmacy management with greater control over fulfillment of the prescription order and over costs associated therewith.

This result is achieved through closely controlled and precise automatic application of patient-specific indicia including patient-specific information to each pre-filled container. Put another way, application of the patient-specific information on the pre-filled container is not indiscriminate as is the case with known automatic information-application systems.

The improvements described herein enable placement of the patient-specific information on the pre-filled container such that the patient-specific information and a selected or predetermined portion of information already on the pre-filled container can be observed and used by the pharmacy personnel. Without such control over information placement, useful information on the pre-filled container would be randomly covered, obscured or impaired by the patient-specific information and thereby rendered unusable. And, this result is accomplished without having to alter the form of the standard or stock pre-filled stock container to ready such pre-filled stock container to receive the patient-specific information.

In a preferred embodiment, an information-application apparatus is utilized to automatically and precisely apply patient-specific information to the pre-filled stock container. Suitable control apparatus is provided to control operation of the information-application apparatus. The control apparatus may be any suitable control or combination of controls.

In certain embodiments, the information-application apparatus is adapted to precisely place a patient-specific label on the pre-filled stock container. A preferred information-application apparatus includes an output device, such as a printer or print engine, and a positioner. The preferred printer is a label printer which generates a label including second indicia including patient-specific information. The printer may apply information to the label in any suitable manner. The positioner directs the pre-filled container to a position for precisely receiving the leading edge of the label so that the label is in the desired position when fully affixed to the pre-filled container. The position in which the pre-filled container is precisely positioned to receive the label or other form of patient-specific indicia is referred to herein as an "indicia-receiving position." The patient-specific label is then applied to the pre-filled container. Application of the label is such that, after label application, the patient-specific information and a predetermined portion of the information on the pre-filled container are observable and available for use.

The positioner component of the information-application apparatus preferably comprises a container gripper and a drive mechanism. The drive mechanism is operative to precisely orient a gripped pre-filled container to receive the label. It is preferred that the information-application apparatus is adapted for use with pre-filled containers that are generally in the form of a cylinder. Examples are bottles and the like. In such embodiments, the drive mechanism comprises a drive roller and a motor in power-transmission relationship with the drive roller. The gripper comprises a pair of idler rollers which are spaced apart from the drive roller. The idler rollers are positionable to urge a pre-filled container against the drive roller such that rotation of the drive roller moves the pre-filled container to the label-receiving position. In this embodiment, the pre-filled container is held in place for application of the label by three points of contact.

In certain embodiments, the information-application apparatus printer comprises a label source, a print element adapted to print the information on a label and a feed mechanism adapted to supply label material to the print element. The feed mechanism, or a separate drive mechanism applies a printed label to a pre-filled container.

Most preferably, the drive roller and pre-filled container form a nip adjacent the printer, and the feed mechanism feeds the printed label into the nip and into contact with the pre-filled container. Rotation of the pre-filled container by the drive roller draws the label into the nip. The adhesive-containing side of the label is urged against the pre-filled container to adhere the label to the pre-filled container.

Preferably, each pre-filled container is identified to the information-application apparatus by means of a reader apparatus. The reader apparatus may comprise one reader or a plurality of readers. The reader reads container-identification information associated with each pre-filled container and communicates that information to the control apparatus resulting in identification of the pre-filled container. Such a reader could be an optical reader adapted to scan a bar code. The reader may also be adapted to identify an RFID transponder including a code representing the pre-filled container contents. The reader apparatus could include one or both of these capabilities or could comprise separate optical and RFID readers.

Following identification, the control apparatus obtains positioning information used to operate the information-application apparatus positioner to position the pre-filled container. The information is preferably in a database accessed by the control apparatus. In embodiments, the database includes positioning information for each pre-filled container enabling the positioner to move the pre-filled container to the label-receiving position. In embodiments, the pre-filled container is positioned relative to a reference point associated with each pre-filled container. The reference point may be any suitable mark, structure (such as a key formed in the pre-filled container bottom surface) or thing. The position of the identified pre-filled container is identified by reference to the reference point. The control apparatus then enables operation of the positioner to position the pre-filled container in the indicia-receiving position.

In certain embodiments, the gripper may be adapted to accommodate a range of different sizes of the pre-filled containers. For example, the gripper can be configured to accommodate pre-filled containers having different circumferences. In such embodiments, it is preferred that the gripper comprises a pair of idler roller supports each of which supports an idler roller. The supports for the idler rollers are movable toward and away from the other to accommodate different pre-filled container circumferences. It is preferred that an actuator moves each support under control of the control apparatus. This arrangement permits the pre-filled container to be positioned so that the label can be received in the nip irrespective of the container circumference.

The control apparatus may be any suitable combination of controls and may include apparatus such as a computer separately and/or in combination with other control components. The control apparatus preferably includes a set of instructions which operate the positioner to move the pre-filled container to the indicia-receiving position, operate the printer to print the second indicia and operate the information-application apparatus to apply the second indicia to the pre-filled container.

The information-application apparatus may be utilized in a variety of configurations including as part of a fully or partially automated prescription fulfillment system or as a stand-alone unit.

BRIEF DESCRIPTION OF THE DRAWINGS

The foregoing and other objects, features and advantages of the invention will be apparent from the following more particular description of preferred embodiments, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
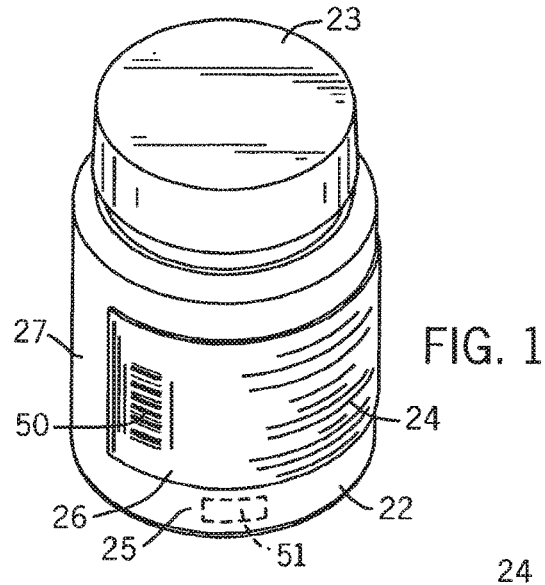
FIG. 1 is a perspective view of an exemplary pre-filled stock container. In the embodiment shown, indicia including information relating to the pre-filled container contents is provided on a label. The information is in stylized form.

Referring first to FIGS. 7-18B, exemplary automatic information-application apparatus 10, 10' and 10" are shown. Information-application apparatus 10, 10' and 10" are adapted to generate a patient-specific label 56 and to precisely place label 56 on pre-filled stock container 22. In general, information application apparatus 10, 10' and 10" comprises an output device, preferably in the form of a label printer (or print engine) 12, together with positioner 14 and controller 16. Throughout the detailed description, like components for each apparatus 10, 10' and 10" are identified by common reference numbers. Positioner 14 preferably comprises container gripper 18, drive mechanism 20 and related components. Gripper 18 and drive mechanism 20 are operative to precisely orient a pre-filled container 22 to receive patient-specific information generated by printer 12.

Referring next to FIGS. 1, 4, 6A and 6B, there are shown representative pre-filled containers 22. Reference number 22 will be associated with each such pre-filled container 22, and such reference number is used to refer to both single pre-filled containers 22 and plural pre-filled containers 22.

A pre-filled container 22 is a container loaded with a medicament, nutriceutical, therapeutic agent or like product or thing. The pre-filled containers 22 are "stock" articles meaning that such pre-filled containers 22 are capable of being used in the same form as provided by the manufacturer, repackager or other supplier without any requirement for modification of the pre-filled container 22 prior to application of patient-specific information. Each such pre-filled container 22 is referred to herein as a pre-filled stock container 22, a pre-filled container 22 or simply as a container 22.

Pre-filled containers 22 are loaded, or pre-filled, with one or more articles or things at the point of manufacture or repackaging. The pre-filled container 22 contents may be in any form and quantity. For example, pre-filled container 22 contents may comprise bulk-form tablets such as capsules, caplets, ellipses, ovals, triangles, balls, multi-angles and the like. Other forms of pre-filled container 22 contents, such as liquids and powders, may be loaded in pre-filled containers 22.

Pre-filled containers 22 typically vary in size and shape. For example, pre-filled containers 22 may be provided in volumetric sizes, such as 75, 120, 200 cubic centimeters. It is preferred that pre-filled containers 22 are provided in a shape which is generally cylindrical. Examples are the pre-filled containers 22 shown in FIGS. 1, 4 and 6A. Exemplary apparatus represented by reference numbers 10, 10' and 10" are configured for use with pre-filled containers 22 having a shape which is generally cylindrical. However, apparatus 10, 10' and 10" may be configured to accommodate other container 22 shapes such as the generally-rectangular shaped pre-filled container 22 shown in FIG. 6B. Containers 22 are typically, but not exclusively, made of plastic materials.

Figure 6A:
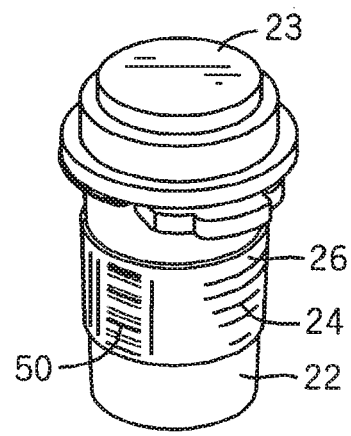
FIGS. 6A and 6B illustrate exemplary alternative forms of pre-filled stock containers.
Figure 6B:
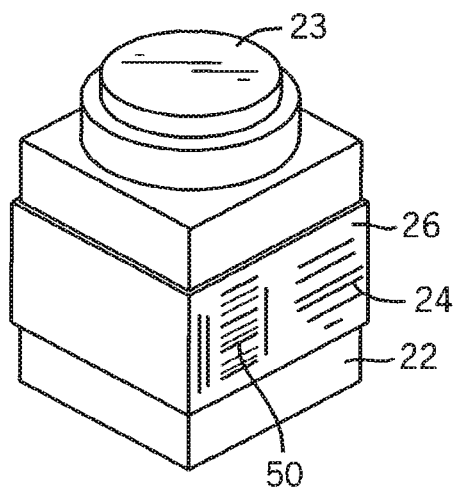

Pre-filled containers 22 include an opening (not shown) through which one or more articles are loaded into each container 22. A removable safety seal (not shown), such as a film or foil seal, may be applied across such container opening after contents of pre-filled container 22 are loaded therein. A cap 23 or other closure is then applied across the pre-filled container opening. Cap 23 can be any suitable type, such as a screw-on cap (FIGS. 1, 4 and 6B) or a snap-fit cap (FIG. 6A). Cap 23 is typically child-resistant and is replaceable over the opening of pre-filled container 22 permitting pre-filled container 22 to be repeatably opened and closed to remove the container 22 contents. A tamper-evident neck seal (not shown) may be applied to or over cap 23.

Referring further to FIGS. 1-2 and 4-6B, pre-filled containers 22 are provided by the manufacturer, repackager or other supplier with indicia 24 to describe the pre-filled container 22 contents and to provide other information important to the pharmacy, care giver, patient and others involved in the distribution chain. Indicia 24 are not limited to any particular type or form, and indicia 24 shown and described herein are merely illustrative. Indeed, the type and form of indicia 24 will vary considerably given the number of products and parties in the distribution chain.

Indicia 24 may be applied to each pre-filled stock container 22 in any suitable manner. One manner of associating indicia 24 with pre-filled container 22 is to apply indicia 24 to an adhesive-backed label 26 affixed to pre-filled container 22. Indicia 24 could be applied in other ways, such as by application directly to outer surface 25. Label 26 may be wrapped fully or partially around outer surface 25 of pre-filled container 22. The label 26 shown in FIG. 1 is wrapped partially around pre-filled container 22 outer surface 25 such that a portion 27 of pre-filled container 22 outer surface 25 is free of contact with label 26.

Figure 2:
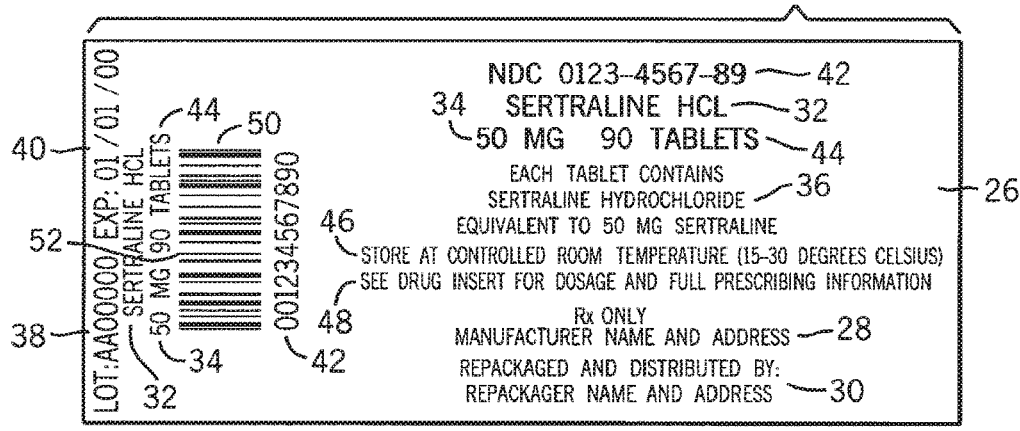
FIG. 2 illustrates the exemplary label of FIG. 1 separate from the pre-filled container. Information relating to the pre-filled container contents is shown.
Figure 4:
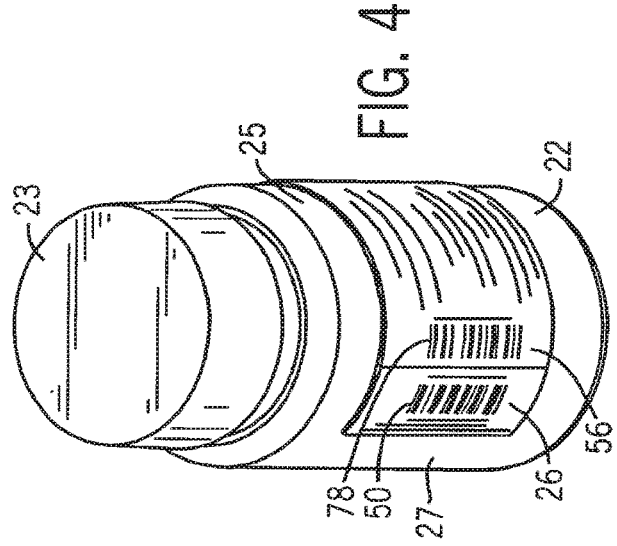
FIG. 4 is a perspective view of the pre-filled stock container of FIG. 1 with the patient-specific label of FIG. 3 precisely positioned thereon. The information is in stylized form.
Figure 5:
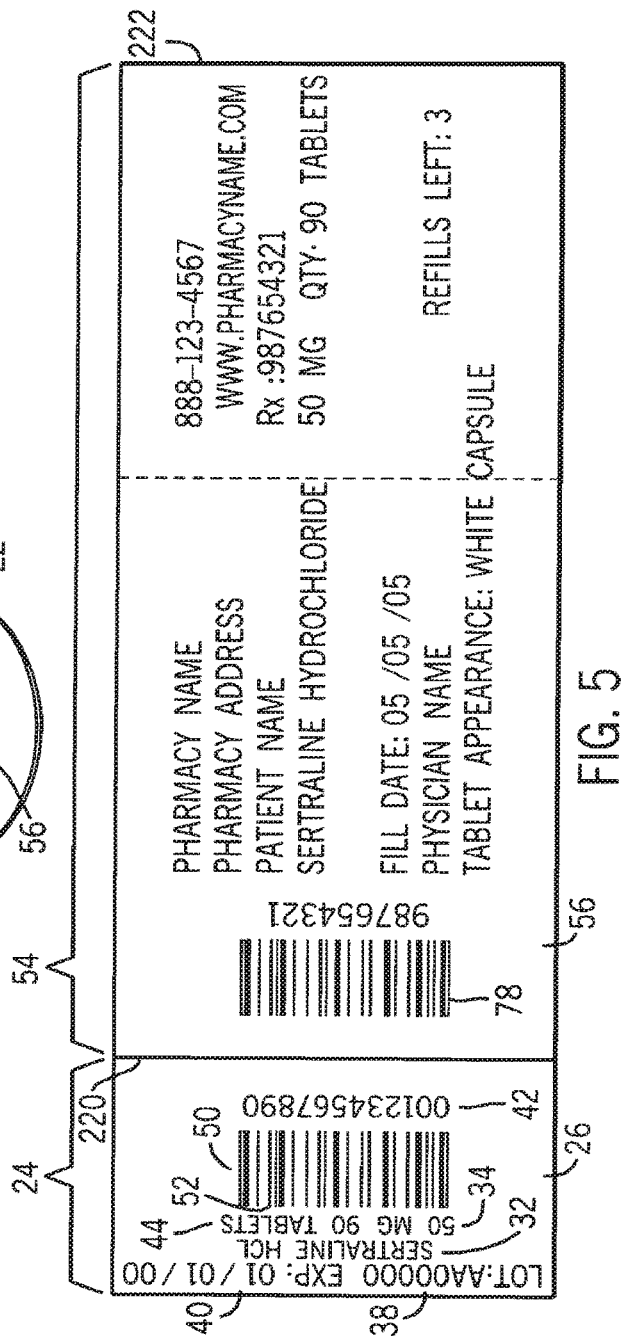
FIG. 5 illustrates the exemplary labels of FIG. 4 but separate from the pre-filled container. Information relating to the pre-filled container contents and the patient's prescription order is shown.

FIGS. 2 and 5 show detail of exemplary indicia 24 associated with the pre-filled container 22 of FIGS. 1 and 4. In the embodiment, indicia 24 are affixed to an adhesive-backed label 26. Among the exemplary information comprising indicia 24 are: the name and address of the manufacturer 28 and/or repackager 30, the type 32, strength 34, description 36, lot number 38, expiration date 40 and quantity 44 of the medication loaded in pre-filled container 22 and a National Drug Code identifier ("NDC") 42. NDC 42 comprises a code which serves as a unique identifier of pre-filled container 22 and its contents. Other information which may comprise indicia 24 includes instructions for handling and storage 46 of pre-filled container 22 and notices 48 relating to the container 22 contents. The U.S. Food and Drug Administration, other regulatory agencies and pharmacies regulate the information provided as indicia 24. As regulations and other demands change over time, indicia 24 associated with pre-filled containers 22 will change to comply with such new regulations and requirements.

Indicia 24 may be in the form of both human-readable information and machine-readable information as shown in FIGS. 1-2 and 4-6B. Human-readable information may include information such as described in connection with reference numbers 28-48. Machine-readable information may include any information or data storage device capable of being read by a machine.

An example of machine-readable information is a bar code 50. Bar code 50 comprises spaced apart light and dark elements. Typical bar code 50 formats include UPC, Code 39, Interleaved 2 of 5 and Code 128. The elements comprising bar code 50 can be read with a bar code scanning device (not shown) to generate a signal corresponding to a code. Representative scanning devices may include a laser scanner or camera. As is known, a bar code 50 acts as an index to a record in a database. Recognition of bar code 50 accesses associated information in the database.

In the example, bar code 50 includes a code corresponding to NDC 42. Scanning of bar code 50, therefore, enables pharmacy management to rapidly and accurately identify the unique signature of pre-filled container 22 and to use that information for any purpose, including to track pre-filled container 22 in inventory and to match pre-filled container 22 to a particular patient prescription order. And, scanning of bar code 50 may be used to control the process of applying patient-specific information to pre-filled container 22 using apparatus 10, 10' and 10" as described herein.

Machine-readable information in combination with, or in place of, bar code 50 can be associated with pre-filled container 22. For example, a two-dimensional ("2D") bar code (not shown) may be used. A bar code in 2D format links to information in a database but also serve as a database including the capability to encode up to several thousand characters of machine-readable data. 2D symbol formats which may be used are PDF417 and Data Matrix symbologies. PDF417 symbologies can be read by laser scanners, cameras, or other instruments using optically sensitive devices such as charge-coupled devices ("CCDs"). Matrix symbols are read by a camera or CCD reader.

A data storage device such as a Radio Frequency Identification ("RFID") tag 51 may be associated with each pre-filled container 22. As is known, an RFID system uses electromagnetic or electrostatic coupling in the radio frequency ("RF") portion of the electromagnetic spectrum to transmit signals. An RFID system comprises a transponder 51 (also referred to as a "tag"), an antenna and a transceiver. Antenna and transceiver may be included as part of reader 86 or as separate components. Tag 51 is an integrated circuit containing RF circuitry and information to be transmitted. The antenna receives the RF. The transceiver reads the RF and transfers the information to a processing device such as computer 104. Tag 51 may be affixed to pre-filled container 22 at any location, not necessarily in a position which can be visually observed from the outside of pre-filled container 22. Tag 51 may be encoded with any suitable information, such as NDC 42. It is expected that the type and form of machine-readable information will evolve over time. Future improvements in such technology are intended to be within the scope of the systems and methods described herein.

Referring to FIGS. 2 and 5, a reference point 52 is provided. Information-application apparatus 10, 10' and 10" utilizes reference point 52 to identify a position of pre-filled container 22 so that pre-filled container 22 can be oriented and located in the indicia-receiving position. Reference point 52 can be a point on label 26 which is at a transition between a light and dark region of label 26, such as the leading edge of bar code 50 as shown in FIGS. 2 and 5 or another mark on pre-filled container 22 or label 26. Reference point 52 could be a mechanical element of pre-filled container 22, such as a key-type indentation or protrusion (not shown) which mates with a key way (not shown) on positioner 14. The manner in which reference point 52 is used to orient pre-filled container 22 to the indicia-receiving position to receive patient-specific indicia 54 is fully described in connection with FIGS. 13C and 14A-14C below.

As can be readily appreciated, indicia 24 or elements of indicia 24 are of immense value to each party in the distribution chain. For example, persons involved in distribution of pre-filled containers 22 may use the information comprising indicia 24 (particularly bar code 50 or tag 51) to track pre-filled container 22 in inventory. Persons involved in fulfillment of patient prescription orders may use the information comprising indicia 24 to select pre-filled container 22, to verify that the medication loaded in pre-filled container 22 is as called for by the prescription and to process payment for the container contents. And, the patient herself will use the information comprising indicia 24 for guidance in taking medication loaded in pre-filled container 22. It is important that the information comprising indicia 24 be accessible for those involved in distribution and use of containers 22.

Figure 3:
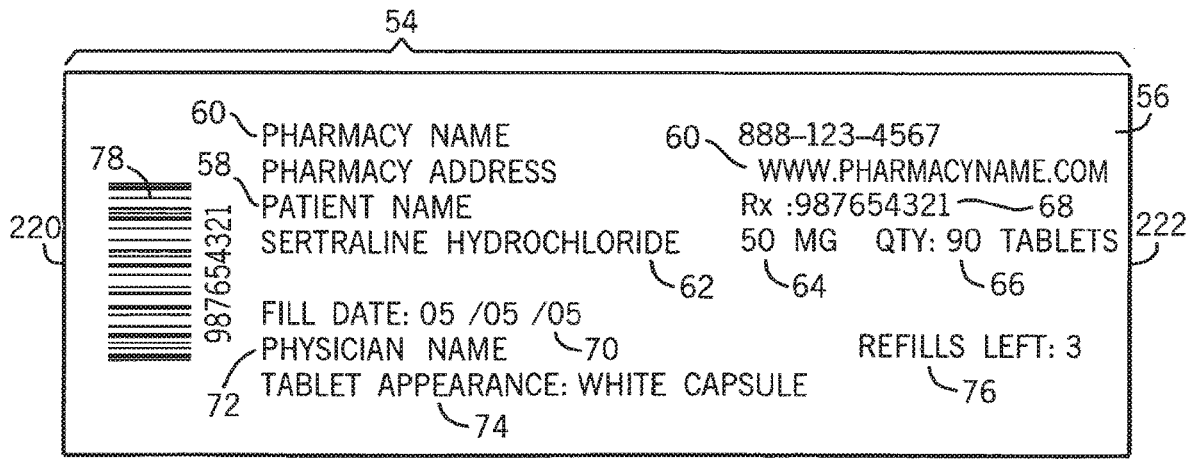
FIG. 3 is an exemplary patient-specific label with indicia including information relating to a patient's prescription order.

A generic pre-filled stock container 22 may be converted for use as a patient-specific container as illustrated in FIGS. 3-5 by applying patient-specific indicia 54 to the pre-filled container 22. The information associated with pre-filled container 22 may be optimized by precise application of the patient-specific indicia 54 as determined by pharmacy management such that indicia 24 are not impaired or obscured and may be read by a human and/or a machine. As shown in the embodiment of FIGS. 3-5, patient-specific indicia 54 are of the type which is affixed to an adhesive-backed label 56 for application over some or all of label 26 and indicia 24 as determined by pharmacy management. Indicia 54 are preferably specific to the patient for whom container 22 is designated.

Among the exemplary information comprising indicia 54 are: the patient name 58, pharmacy name, street address, Internet address and telephone number 60, the type 62, strength 64, quantity 66 of the medication, the prescription number 68, fill date 70, physician name 72, a text description or image of the appearance of the container contents 74 and refill information 76. And, indicia 54 may include one or more types of machine-readable information, such as a bar code 78 of the types described herein. An RFID tag (not shown) of the type described in connection with tag 51 may be affixed to label 56 and associated with patient-specific indicia 54. Such bar code 78 or other information may be used to uniquely associate pre-filled container 22 with a specific patient prescription order by computer 104 and database 106. Pharmacy Boards regulate the information included in indicia 54. As regulations change in the future, the information comprising indicia 54 would be expected to change to comply with new regulations.

Figure 15:
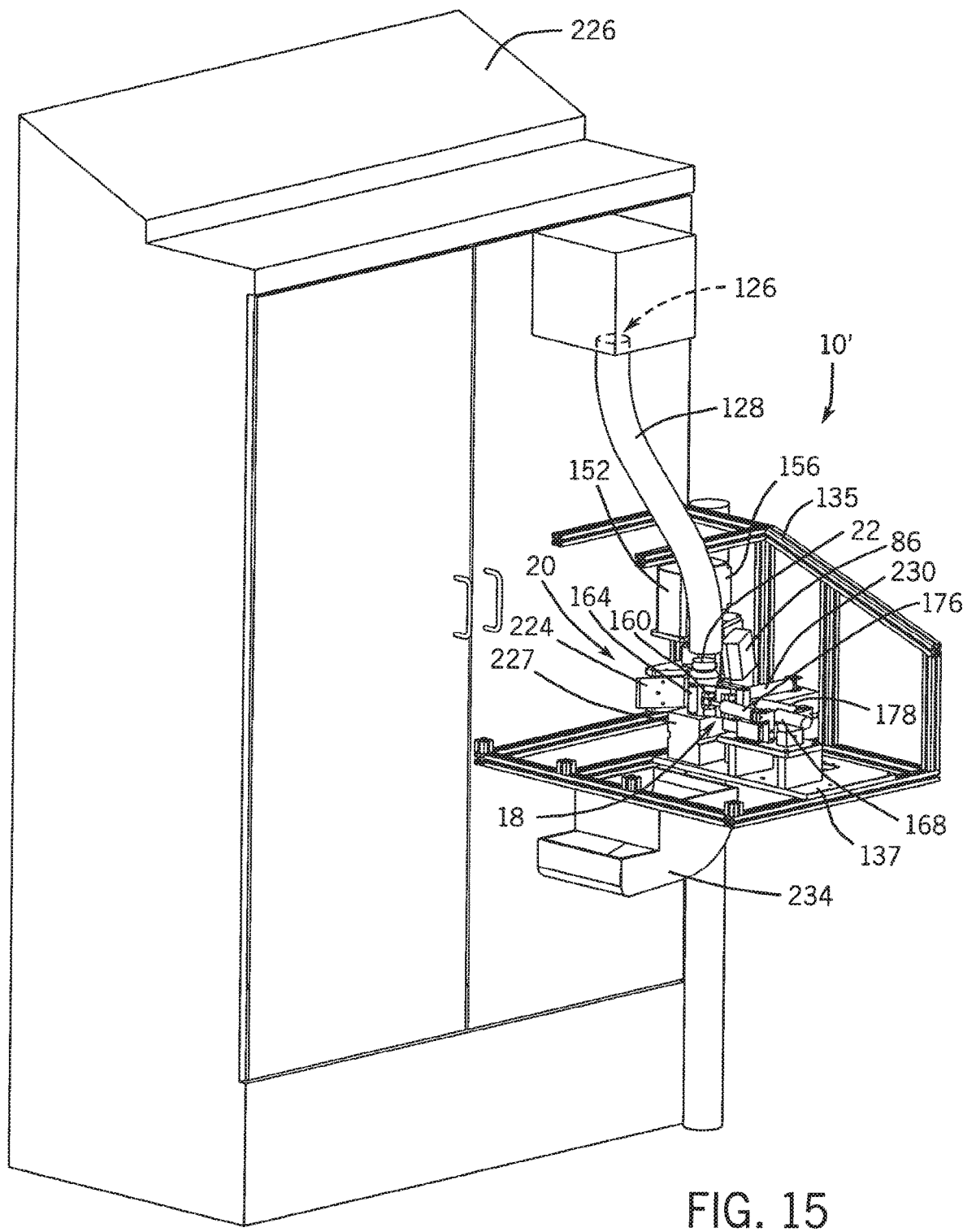
FIG. 15 is a perspective view of an alternative embodiment of an exemplary information-application apparatus shown mounted to an automatic dispenser. Certain parts are cut away to facilitate understanding of the apparatus.
Figure 16:
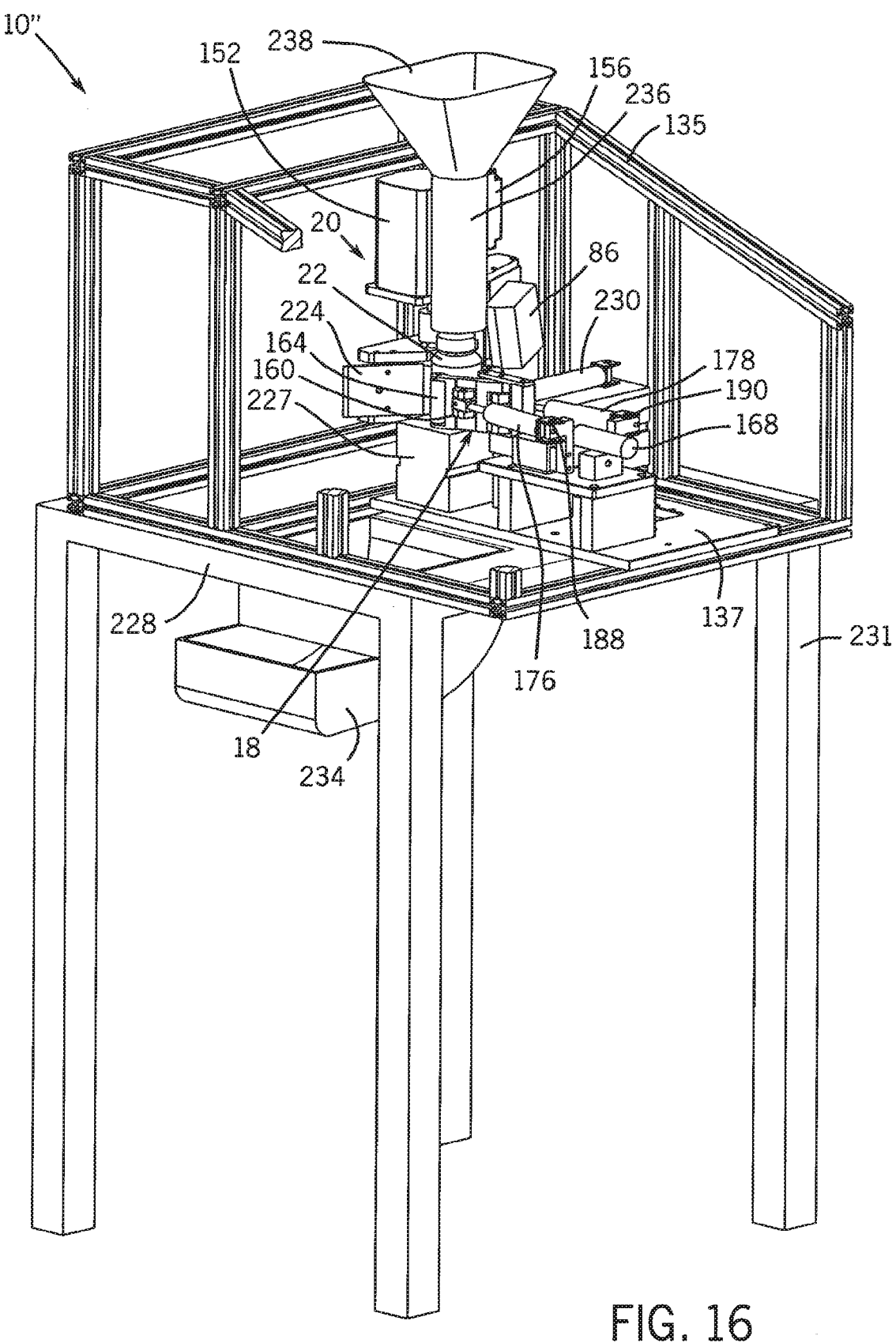
FIG. 16 is a perspective view of a further alternative embodiment of an exemplary information-application apparatus shown as a stand-alone apparatus. Certain parts are cut away or not shown to facilitate understanding of the apparatus.
Figure 17:
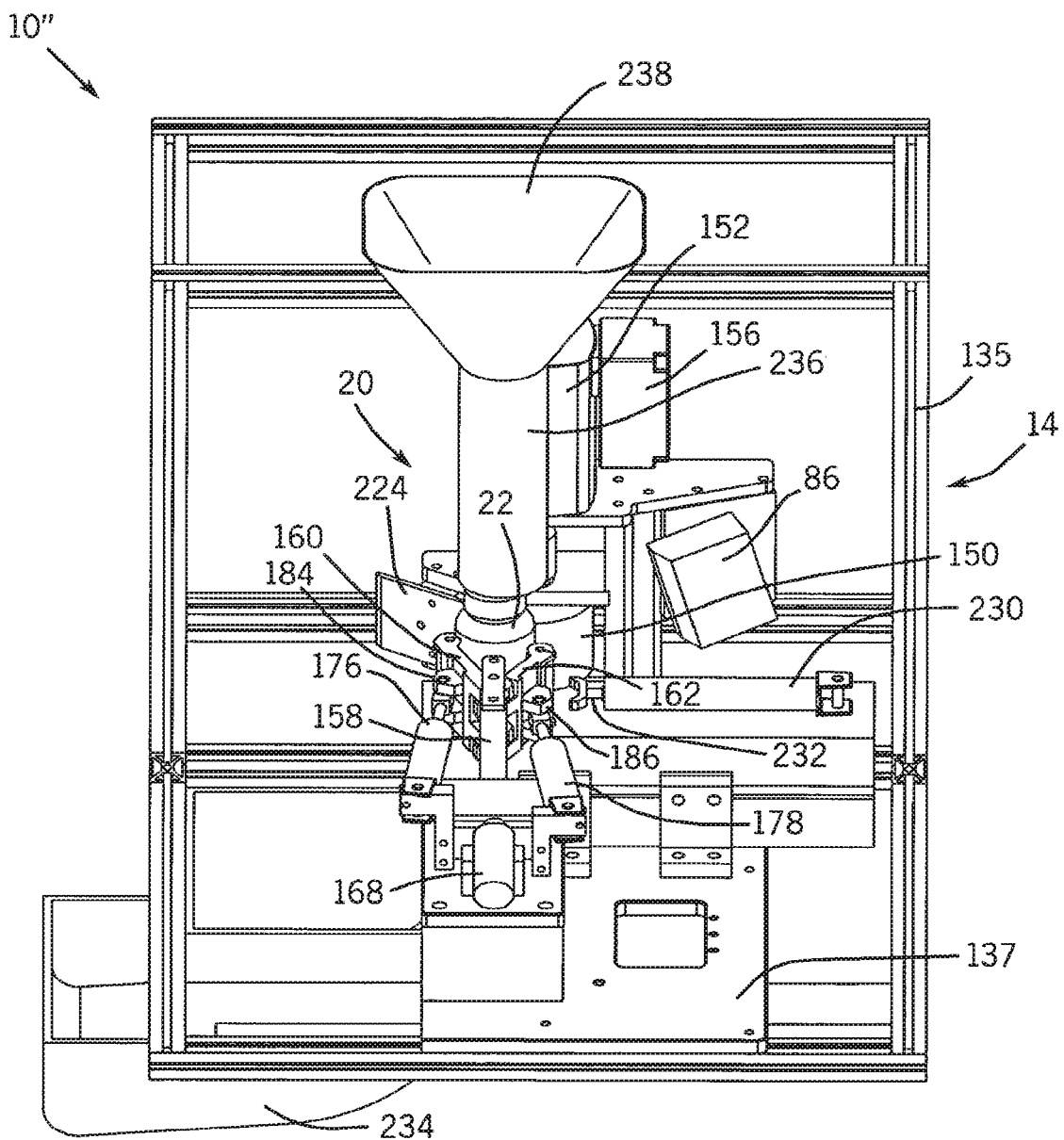
FIG. 17 is a perspective view of the embodiment of FIG. 16. Certain parts are cut away or not shown to facilitate understanding of the apparatus.

Referring next to FIGS. 7-13G, information-application apparatus 10 will be described in the context of an automated workflow management system ("WMS") 80. As illustrated and described in connection with FIGS. 15-18B, information-application apparatus 10 may be used in applications other than system 80. For example, apparatus 10' is shown in combination with an automatic dispenser 226 (FIGS. 15 and 18A) while apparatus 10" is configured for use as a stand-alone unit (FIGS. 16-17 and 18B). Information-application apparatus 10' and 10" are essentially identical to apparatus, particularly with respect to printer 12 and positioner components 14 and it will be understood that the description of apparatus 10 also applies to information-application apparatus 10' and 10".

Figure 7:
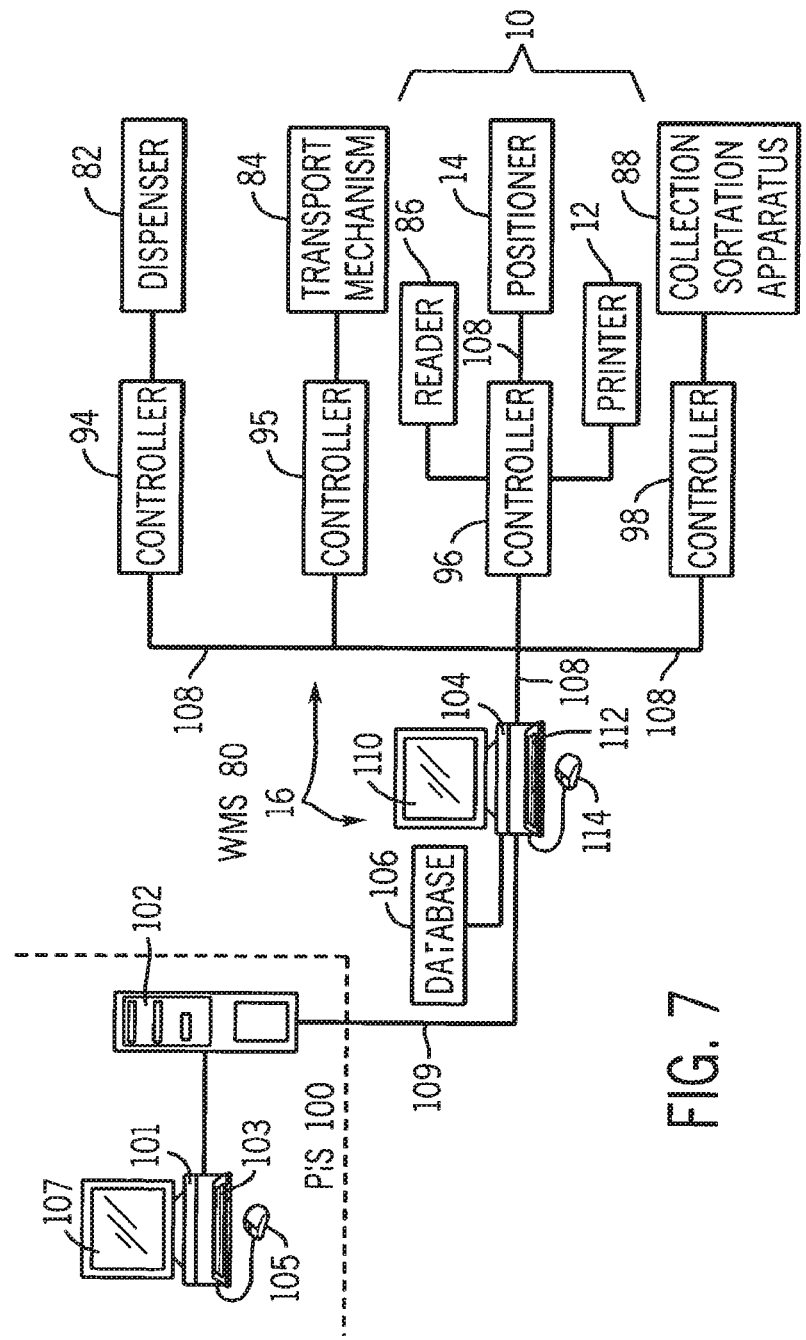
FIG. 7 is a schematic illustration showing components of an exemplary dispensing system including an exemplary information-application apparatus.

System 80 illustrated schematically in FIG. 7 represents an automated WMS for use in processing patient prescription orders. System 80 comprises plural automated components including container dispenser 82, container transport mechanism 84, information-application apparatus 10 (including printer 12, positioner 14 and reader 86), container collection and sortation apparatus 88, and control apparatus 16 for controlling operation of such components.

Referring more specifically to FIG. 7, system 80 includes a container dispenser 82, a container transport mechanism 84, information-application apparatus 10 (including reader 86, positioner 14, and printer 12) and a container collection and sortation apparatus component 88. Control apparatus 16 controls operation of components 82, 84, 10 and 88. Control apparatus 16 comprises computer 104 and controllers 94, 95, 96 and 98. Interface 108 is provided for transmission of information between computer 104 and one or more of controllers 94, 95, 96 and 98 and components 82, 84, 10 and 88.

Computer 104 includes display 110, keyboard 112 and mouse 114 to permit pharmacy management to interact with system 80. Computer 104 may run a prescription processing software program such as PPS from AutoMed Technologies, Inc. of Vernon Hills, Ill. The PPS software residing on computer 104 enables operation of system 80 and provides information required to initiate, for each container 22 pertaining to a prescription order, the automatic process of: dispensing, transporting, applying information and sorting and collecting. The PPS software manages operation of all components of the system 80 for fulfillment of patient prescription orders.

A database 106 identifying pending prescription orders and each pre-filled container 22 used in system 80 resides on computer 104. Database 106 includes information uniquely identifying each of the pre-filled containers 22 by means of a machine-readable code, such as bar code 50 or an RFID tag 51. Database 106 also includes, for each pre-filled container 22, information necessary to precisely position container 22 for precise application of patient-specific indicia 54 to container outer surface 25 as described in full detail below. Database 106 may include other information of use to pharmacy management, such as a complete record of all prescription orders filled by system 80.

Controllers 94, 95, 96 and 98 are provided to enable operation of the corresponding component or components 82, 84, 10 and 88 of system 80. Controllers 94, 95, 96 and 98 may, for example, be programmable logic controllers ("PLC"). Representative PLCs for use as controllers 94, 95, 96, 98 are Allen-Bradley® Micrologix PLCs available from Rockwell Automation of Milwaukee, Wis. Controllers 94, 95, 96 and 98 may comprise other types of controls, for example, one or more microcontrollers (not shown) associated with the information-application apparatus 10 or other components 82, 84, 86, 88. The functions of controllers 94, 95, 96, 98 may be combined into fewer or more hardware elements as determined by the system manager.

System 80 may be scaled, configured and arranged as required by pharmacy management. Such requirements may be based on the patient population served by system 80, required prescription order processing throughput, available floor space and cost considerations.

As shown schematically in FIG. 7, system 80 may optionally receive prescription orders for fulfillment from a Pharmacy Information System ("PIS") 100. If utilized, PIS 100 processes patient prescription orders and releases those orders for fulfillment by system 80 following completion of desired processes, such as patient data entry, drug utilization review and adjudication.

PIS 100 includes information-management software residing, for example, on computer 102. The information-management software residing on computer 102 may be a standard, commercially-available database engine or other information-storage software which provides functions, such as administrative and accounting functions.

A patient prescription order is initially presented to pharmacy personnel by a patient or other person. Data pertaining to the prescription order is entered into computer 102 of PIS 100 using any suitable user interface, such as a client computer 101, keyboard 103, mouse 105 and display 107. Data entered typically will include, for example, patient name, the type, strength, quantity of the medication, prescriber information (e.g. physician name), payor information, refill information and instructions regarding the prescription. Computer 102 may automatically associate other information with the prescription order, such as the pharmacy name, street address, pharmacy Internet address and telephone number, prescription number, fill date and a text description or image of the appearance of the container contents. PIS 100 computer 102 typically maintains a database of information on each patient.

Following data entry, software residing on computer 102 is preferably utilized to conduct a drug utilization review ("DUR") and to adjudicate any claim with insurance or other third-party payor. Following any DUR and adjudication, the patient prescription order is sent (for example as a data packet) from computer 102 to computer 104 via interface 109. Interface 109 may include any suitable information-transmission capability including modem, local area network ("LAN"), Internet and combinations thereof. PIS 100 and computer 102 may be co-located with system 80 and computer 104 at the same site or may be located at completely separate sites as required by pharmacy management.

Figure 8:
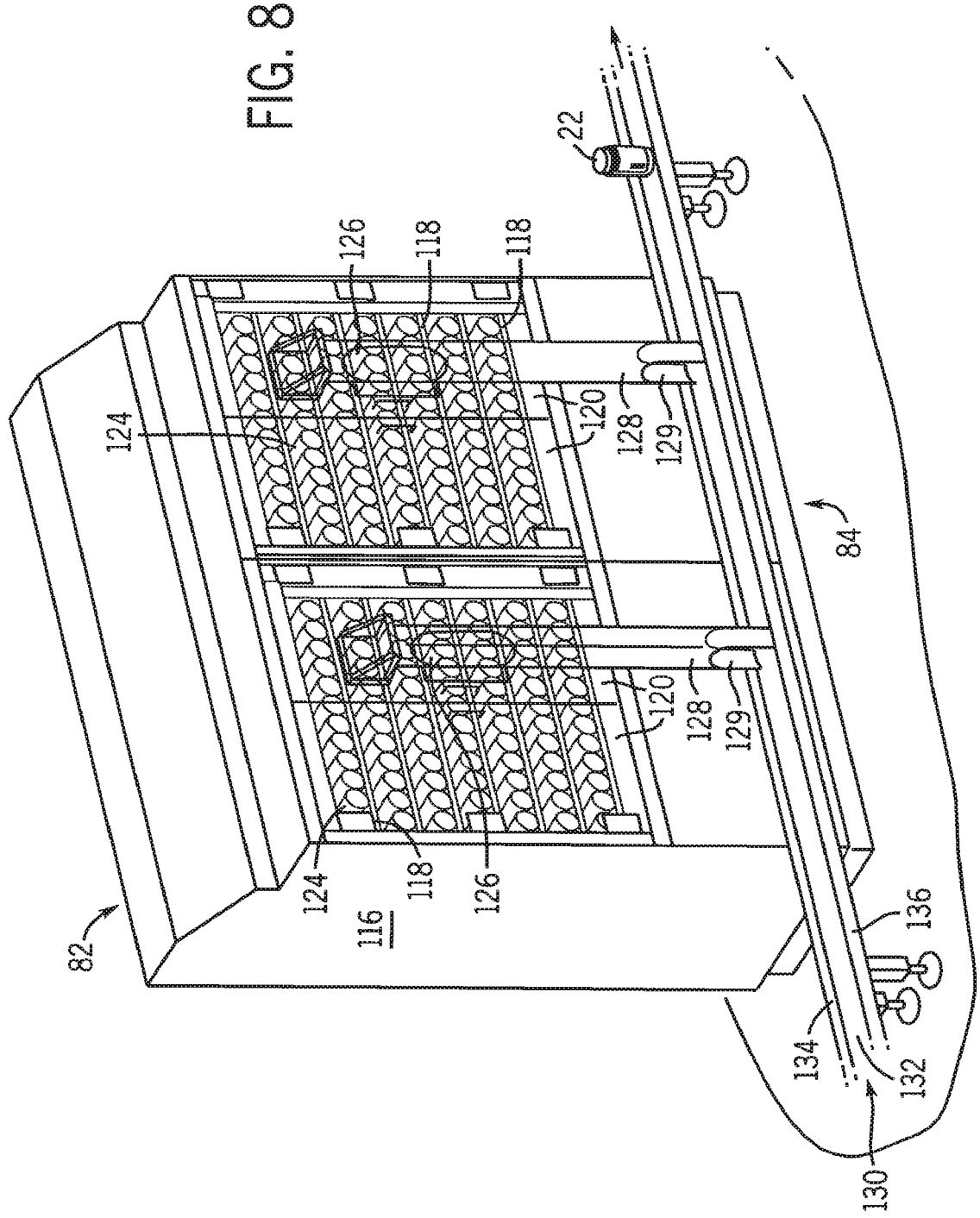
FIG. 8 is a perspective view of an exemplary automatic pre-filled container dispenser.
Figure 9:
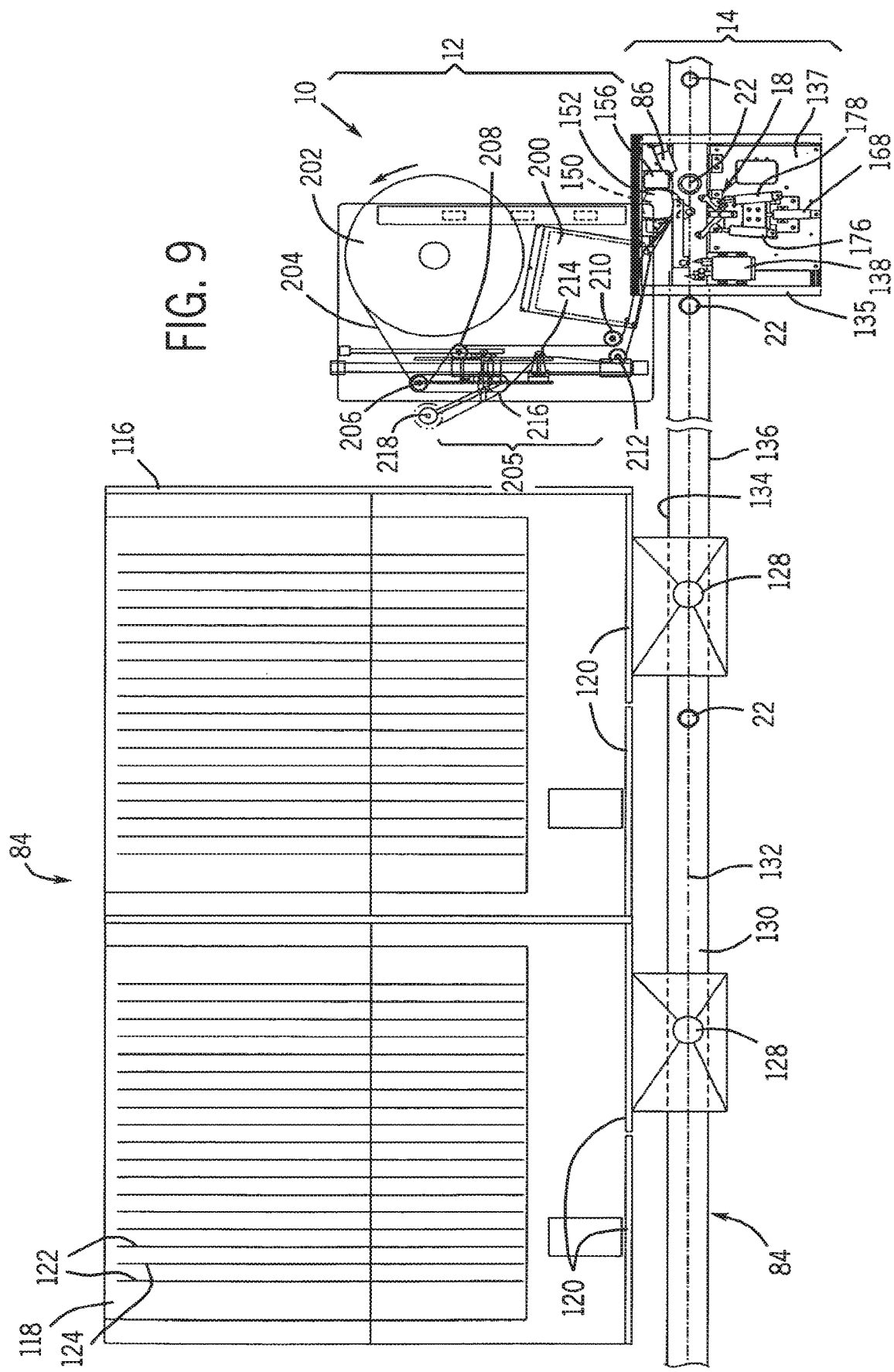
FIG. 9 is a schematic illustration showing components of an exemplary system including exemplary dispenser, container transport and information-application apparatus.

Referring now to FIGS. 7-9, automatic dispenser 82 is provided to store and to dispense one or more pre-filled stock containers 22 from a stock or inventory of pre-filled containers 22 as required to fulfill each patient prescription order. Referring to FIGS. 8 and 9, dispenser 82 includes a housing 116 enclosing a plurality of storage shelves of which shelf 118 is representative. Housing 116 is preferably fabricated from aluminum, stainless steel or plastic to be fully compatible with a pharmacy setting. Housing 116 may include transparent doors 120 which open and close to permit access to dispenser 82 for loading of pre-filled containers 22 onto shelves and to service the dispenser 82.

Each shelf (e.g., 118) includes suitable vertically-oriented walls 122 which organize pre-filled containers 22 into rows, such as row 124. Each row contains one type of pre-filled container 22. The shelves, such as shelf 118, may be downwardly angled such that gravity causes containers 22 in each row to slide toward the front of dispenser 82.

Each row (e.g., row 124) defines a separate shelf location known to the PPS software residing on computer 104 and identifiable to controller 94 and dispenser 82 by a unique position in an x, y, z coordinate system. The unique position of each shelf location and the inventory of pre-filled containers 22 at each shelf location is stored in the PPS database 106 residing on computer 104. In addition, each shelf location may be indicated by a unique machine and/or human-readable code (not shown) located proximate each row, such as row 124. The shelf-associated code may be a bar code, RFID tag or other suitable symbology. The code may be used to track pre-filled container 22 from its row.

Dispenser 82 controller 94 receives a signal via interface 108 from computer 104. Controller 94 interprets the signal sent from computer 104 and enables dispenser 82 to automatically operate to dispense a pre-filled container 22 as required by the patient prescription order. For example, controller 94 may enable operation of a dispenser transport mechanism (not shown) to transport the requested pre-filled container 22 from its shelf location to a position for discharge from the dispenser 82. Such a dispenser transport mechanism may be configured to move in an x, y, z coordinate system between doors 120 and the shelves (e.g., 118) to the appropriate shelf location. A gripper (not shown) may be associated with the dispenser transport mechanism and such gripper may grip the lowermost pre-filled container 22 in the selected row. The dispenser transport mechanism then places pre-filled container 22 through chute upper opening 126 into chute 128. Pre-filled container 22 falls by means of gravity down chute 128 and through chute lower opening 129 for transport by the container transport mechanism 84 to information-application apparatus 10.

As each pre-filled container 22 is dispensed, a signal is sent by dispenser 82 to computer 104 via interface 108. Database 106 is updated to indicate that the pre-filled container 22 corresponding to each prescription order then being fulfilled has been dispensed and is in route to the information-application apparatus 10. The sequence in which pre-filled containers 22 are dispensed from dispenser 82 may be recorded in database 106 to facilitate this process of matching each pre-filled container 22 to a specific patient prescription order.

The size, capacity and type of automated dispenser 82 utilized will typically vary depending on the throughput and other needs and requirements of pharmacy management. An exemplary dispenser 82 suitable for use in system 80 is the FastFind® system available from AutoMed Technologies. A FastFind dispenser may be modified to discharge pre-filled containers 22 stored therein simply by affixing chute 128 thereto and directing pre-filled containers 22 to the chute 128 upper opening 126.

FIGS. 7-13G illustrate a container transport mechanism 84 for transporting pre-filled containers 22 from dispenser 82 to information-application apparatus 10. Preferred transport mechanism 84 comprises an endless conveyor 130. Conveyor link chain 132 is powered by a motor drive (unshown) to transport pre-filled containers 22 from or to components 82, 10 and 88. Drive unit is enabled for operation by controller 95. Controller 95 receives a signal via interface 108 from computer 104 and interprets the signal to enable operation of the drive unit to power conveyor link chain 132 at a desired rate of movement. Guide rails 134, 136 are provided adjacent link chain to direct pre-filled containers 22 along the conveyor 130.

Conveyor 130 may be of any suitable type and may be arranged in any suitable configuration to meet the requirements of the pharmacy management. For example, conveyor 130 may be a single-direction conveyor or a recirculating conveyor. Conveyor 130 may include single or multiple lines arranged in series or in parallel. Container-transport mechanism 84 may be of types other than conveyor 130 and may comprise, for example, a walking beam conveyor or a robotic transport apparatus configured to transport a single pre-filled container 22 to the information-application apparatus 10.

A representative conveyor 130 suitable for use as container transport mechanism 84 is a Simpli-Flex® modular conveyor system available from Simplimatic Automation of Lynchburg, Va. The Simpli-Flex system is useful, at least in part, because it can be easily scaled and configured to meet the specific throughput and spacial requirements of pharmacy management and because it includes a wide range of link chains 132 which can be adapted to transport virtually any type of pre-filled container 22.

FIGS. 9-13G illustrate information-application apparatus 10 and related components. In the embodiment, information-application apparatus 10 is configured to precisely apply a patient-specific label 56 to the pre-filled container 22 and to do so in a way which optimizes the value of indicia 24 provided with pre-filled container 22.

Referring further to FIGS. 9-13G, information-application apparatus 10 preferably includes housing 135 (FIG. 9), base 137 and an escapement device 138 secured to base 137. Escapement device 138 is enabled for operation by controller 96 responsive to a signal from computer 104 via interface 108 to singulate movement of pre-filled containers 22 toward positioner 14. In the example, escapement device 138 includes first 140 and second 142 stops and container sensor 144. Wedge-shaped stop ends 146, 148 enable the stops 140, 142 to slide easily between adjacent containers 22 and to separate adjacent containers 22 from one another thereby facilitating singulation.

Figure 10:
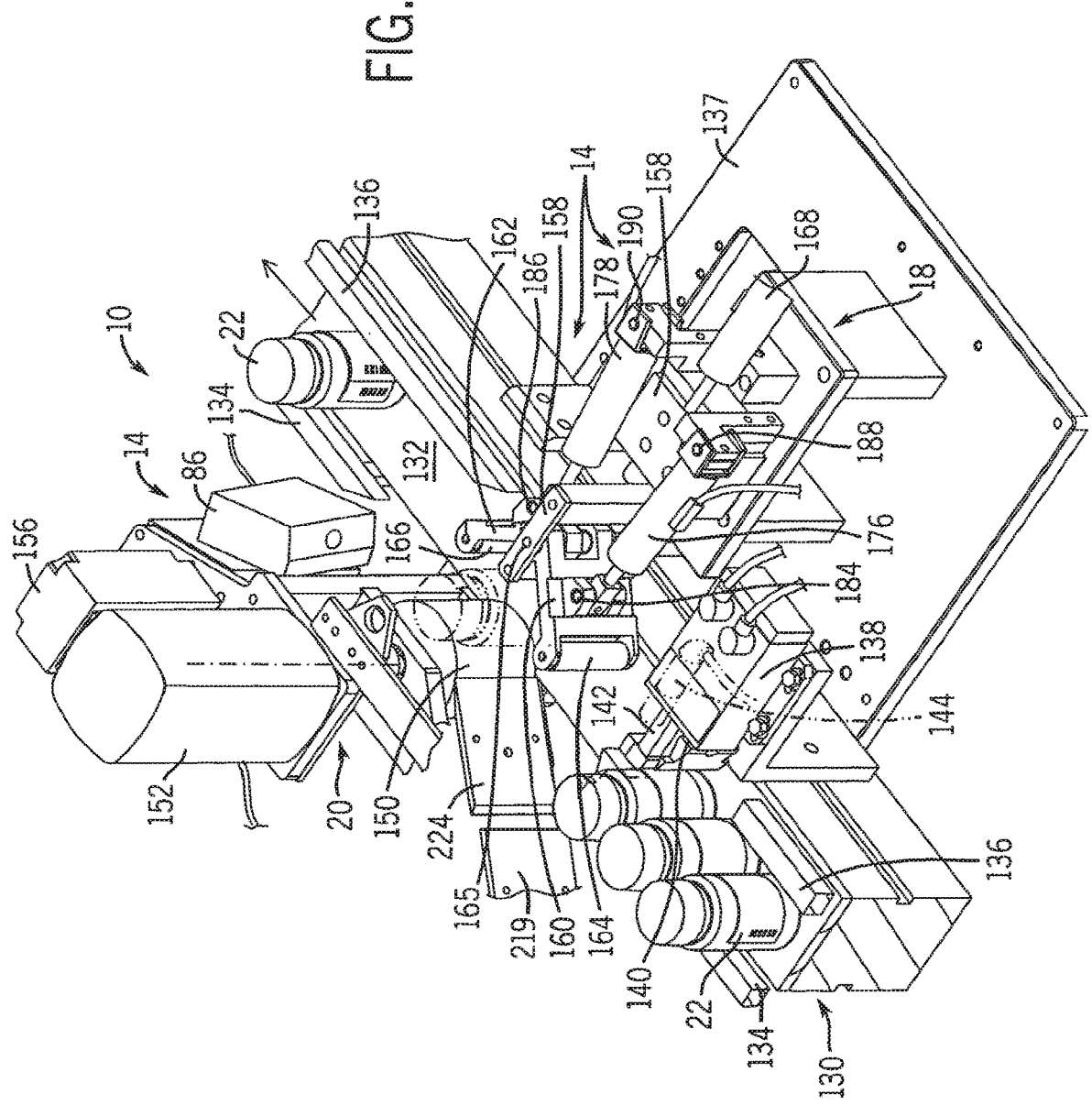
FIG. 10 is a perspective view of an exemplary information-application apparatus and a portion of a container transport mechanism. Components of a positioner apparatus and a printer apparatus are shown. Certain parts are shown in dotted line or are not shown to facilitate understanding of the apparatus.
Figure 11:
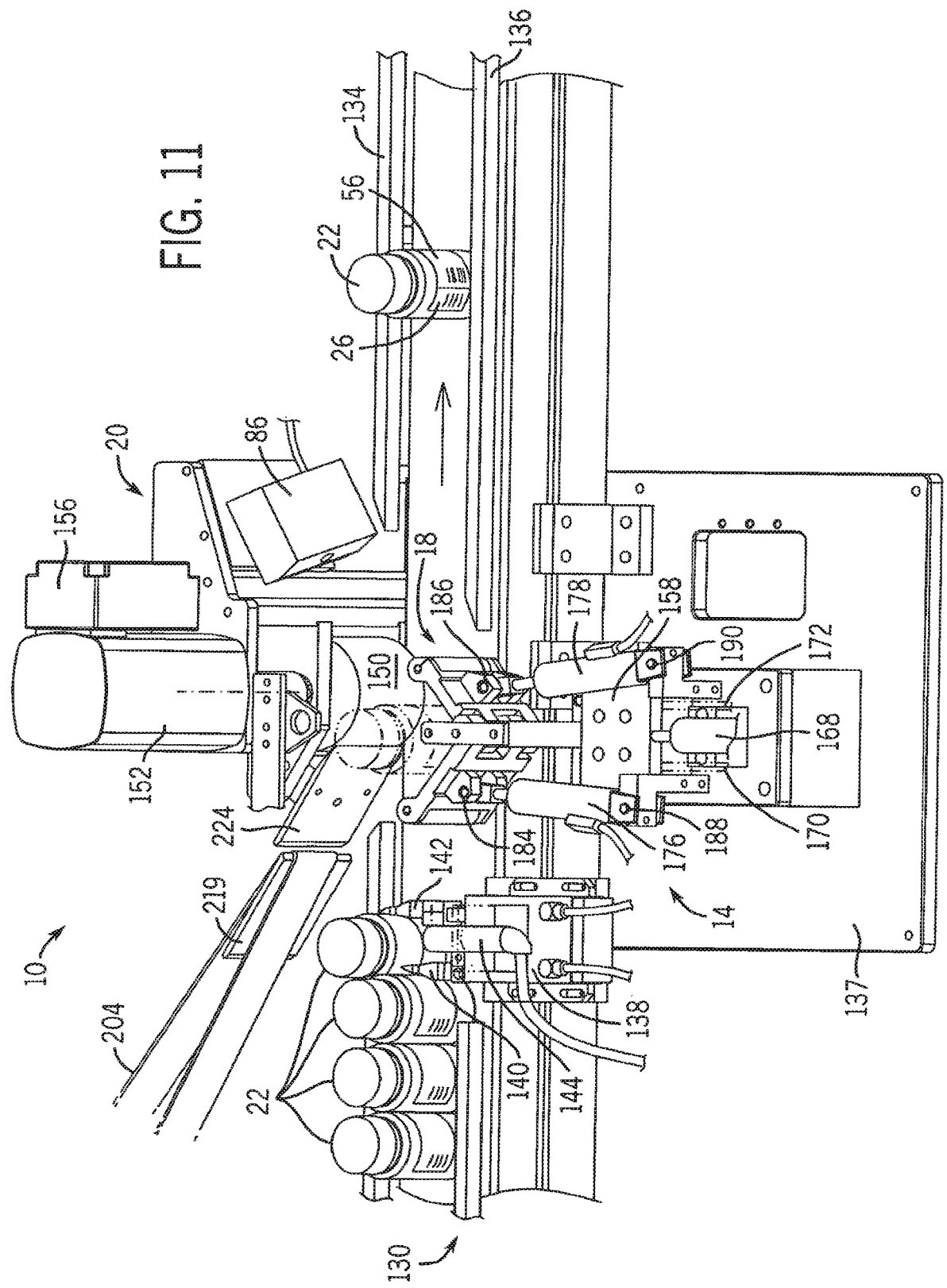
FIG. 11 is further perspective view of the information-application apparatus of FIG. 10.
Figure 12:
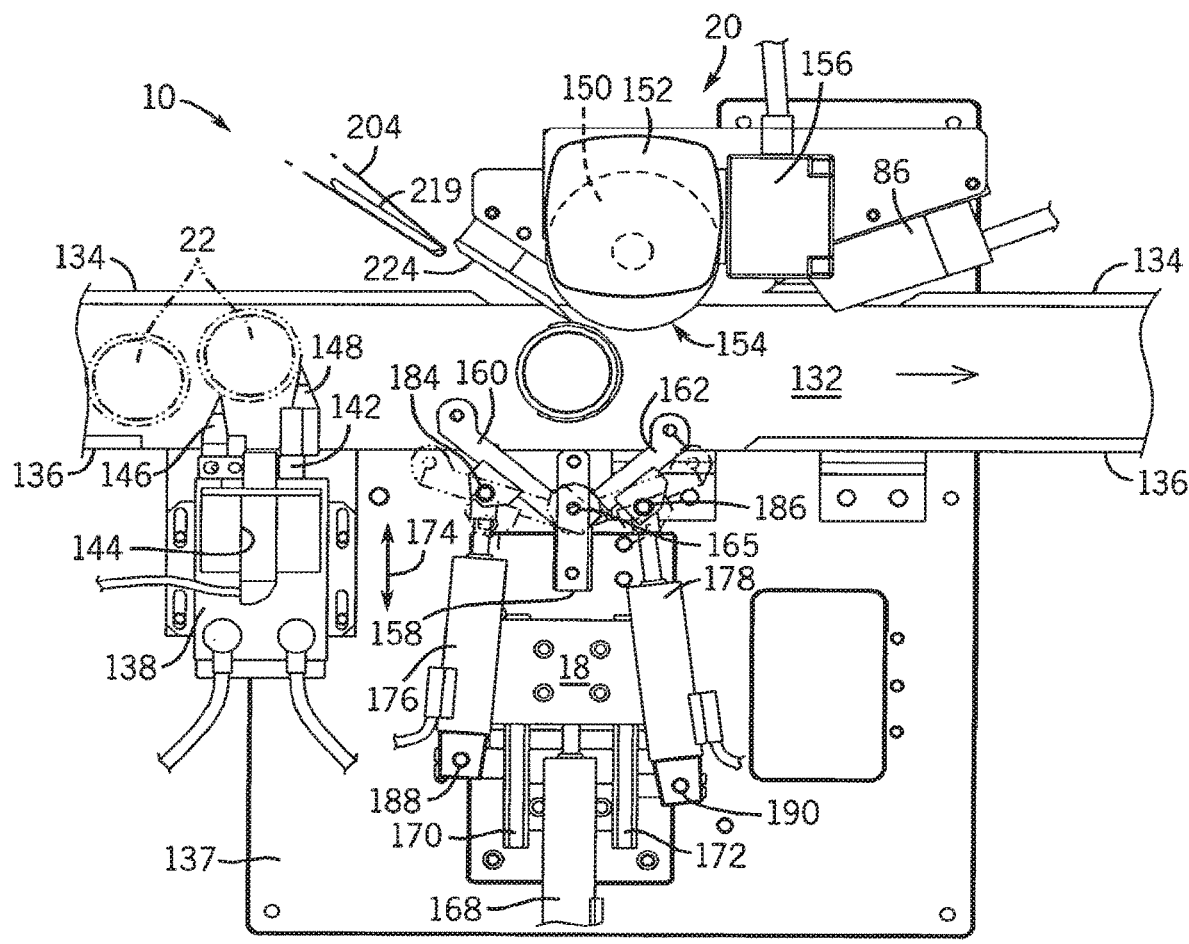
FIG. 12 is further perspective view of the information-application apparatus of FIG. 10.

A suitable actuator (not shown) enabled for operation by controller 96 alternately extends and retracts stops 140, 142 between the container-stop position in FIGS. 10-12 and the container-release position shown in FIG. 9. The escapement device 138 actuator may comprise, for example, rack and pinion arrangement (not shown) in which a bi-directional motor powers a pinion gear meshed with racks associated with each stop 140, 142. Rotation of the pinion gear in one direction retracts stop 140 and extends stop 142, while rotation in a second direction extends stop 140 and retracts stop 142.

Initially, stop 140 is retracted and stop 142 is extended as shown in FIGS. 10-12. Stop 140 blocks movement of all adjacent pre-filled containers 22 and guide rails 134, 136 constrain arrangement of the pre-filled containers 22 into the form of a single file row as shown in FIGS. 10-12. In the embodiment, conveyor 130 link chain 132 continues to move, sliding beneath pre-filled container 22 or containers stopped by escapement device 138 (see FIGS. 10-12).

Sensor 144 generates a signal for controller 96 and computer 104 when a held container 22 is proximate sensor 144. Sensor 144 is preferably a photodetector operatively connected to controller 96 and computer 104 via interface 108. Preferably, each pre-filled container 22 held by escapement device 138 and proximate sensor 144 is known to computer 104 through updating of database 106 as pre-filled containers 22 are dispensed from dispenser 82 and are processed by information-application apparatus 10.

A held pre-filled container 22 is released to positioner 14 of information-application apparatus 10 when controller 96 generates a signal causing stop 140 to extend and stop 142 to retract. Wedge-shaped end 146 easily slides between adjacent containers 22 when extended thereby enabling only one pre-filled container 22 to move past. The process of extension and retraction of stops 140, 142 is repeated for each cycle such that each pre-filled container 22 is delivered one-by-one to positioner 14.

Referring now to FIGS. 10-13G, pre-filled containers 22 are positioned for receiving a patient-specific label 56 by positioner 14. Positioner 14 includes a container gripper 18, drive mechanism 20 and related components. Drive mechanism 20 is operative to precisely orient a gripped, pre-filled container 22 to receive patient-specific label 56. Positioner 14, gripper 18 and drive mechanism 20 are enabled for operation by controller 96.

In the embodiment, information-application apparatus 10 is adapted to orient pre-filled containers 22 having a generally cylindrical shape, such as that shown in FIGS. 1, 4 and 6A. Drive mechanism 20 includes a drive roller 150 and a motor 152. Drive roller 150 is a generally cylindrically-shaped roller with a frictional outer surface 154 provided to positively engage and spin a pre-filled container 22 clamped against drive roller 150 as described herein. Drive roller surface 154 may comprise any suitable material capable of positive engagement with outer surface 25 of pre-filled container 22. A surface 154 formed of a resilient, elastomeric material is preferred.

Drive roller 150 is mounted to a motor axle (not shown) and may be in a direct drive relationship with motor 152. Motor controller 156 is operatively connected to controller 96 under control of the PPS residing on computer 104. As can be appreciated, motor 152 may be in any power-transmission relationship with drive roller 150. For example, motor 152 may power drive roller 150 through a suitable gear train (not shown).

As shown in FIGS. 9-13G, gripper 18 is configured to clamp a pre-filled container 22 against drive roller 150. Rotation of drive roller 150 spins the clamped pre-filled container 22 for container identification and verification and for precise application of the patient-specific information 54 on pre-filled container 22.

Gripper 18 shown herein preferably includes a mechanical linkage that allows it to accommodate a range of pre-filled containers 22 with diameters that differ and to position such pre-filled containers 22 in the proper indicia-receiving position for application of the patient-specific label 56 without requiring installation of a separate gripper 14 or gripper part. This feature allows pharmacy management to process a more diverse range of prescriptions through information-application apparatus 10.

Gripper 18 includes a gripper member 158, a pair of idler roller supports 160, 162 pivotally mounted on member 158 at joint 165 and a pair of unpowered idler rollers 164, 166 journaled on a respective support 160, 162. Joint 165 enables supports 160, 162 to pivot toward and away from each other and drive roller 150 to capture and securely clamp a pre-filled container 22 against drive roller 150 with three points of contact.

Figure 13A:
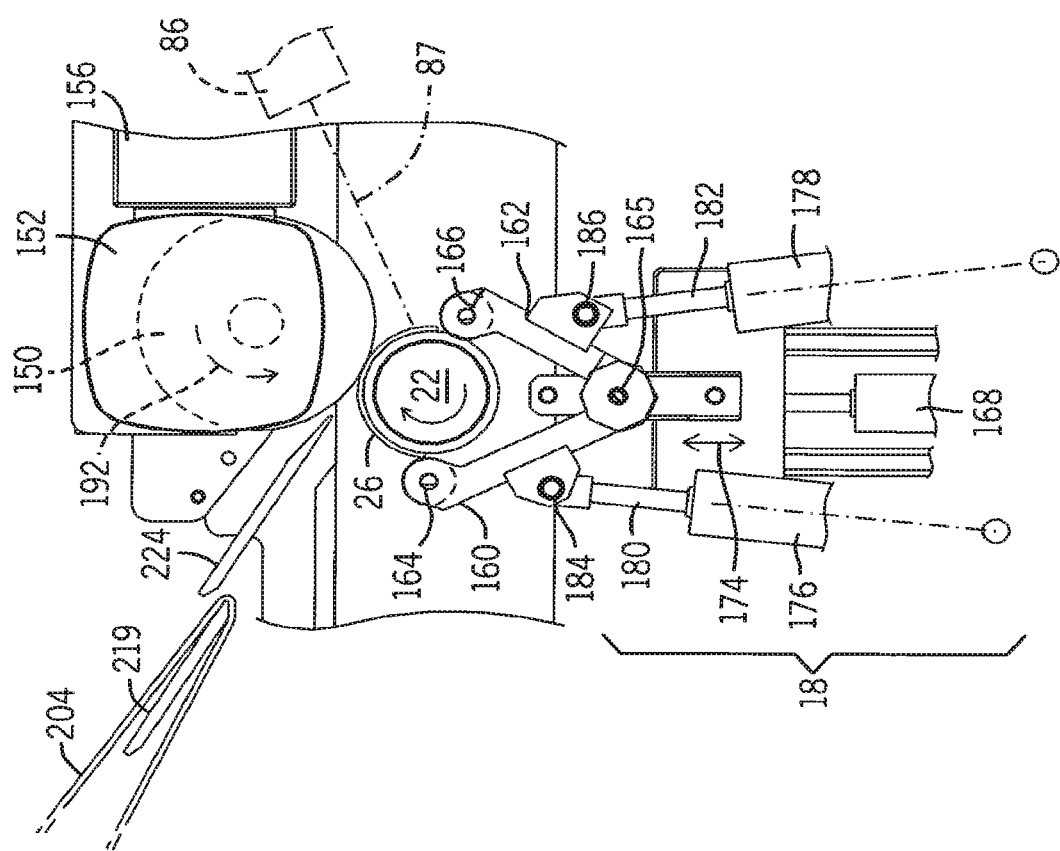
FIG. 13A is a schematic illustration of the information-application apparatus of FIG. 10 shown in a position receiving a pre-filled container.
Figure 13B:
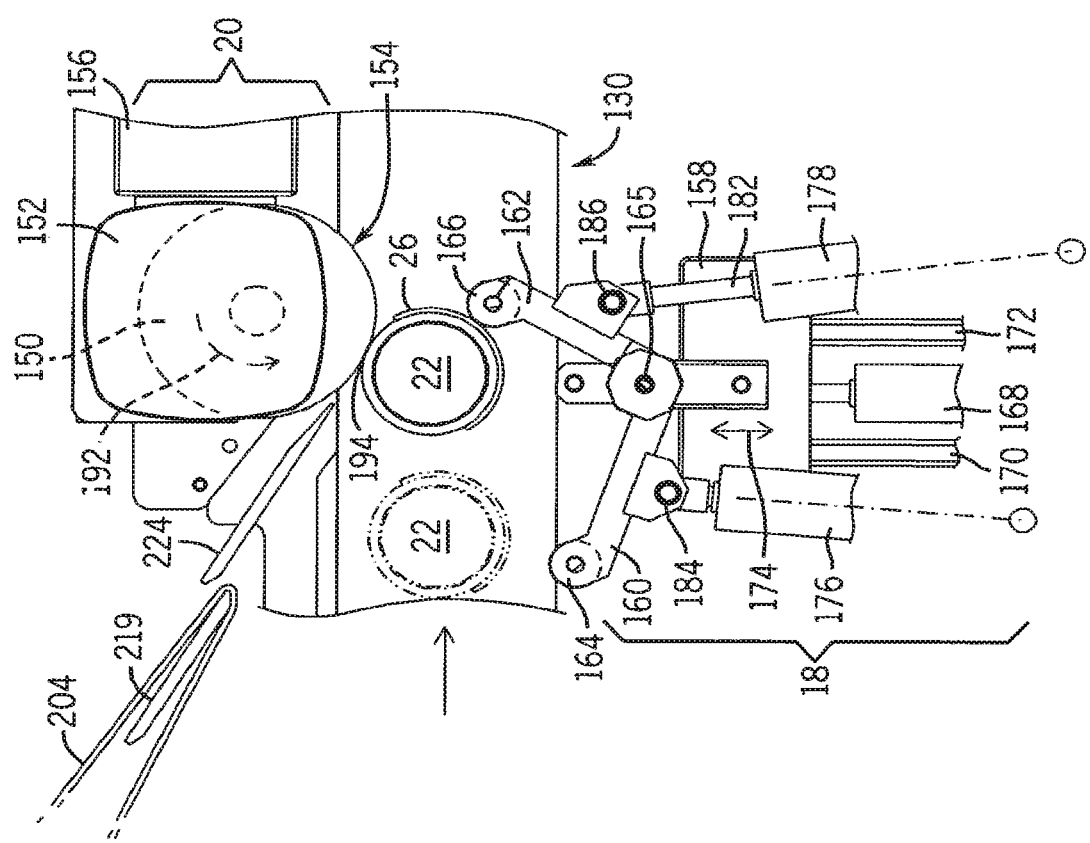
FIG. 13B is a further schematic illustration of the information-application apparatus of FIGS. 10 and 13A shown in a position identifying the pre-filled container before application of patient-specific information thereto.

A dual-acting, air-powered linear actuator 168 extends and retracts member 158. Member 158 is mounted on guides 170, 172. Member 158 translates toward or away from drive roller 150 along guides 170, 172 alternately in the directions of dual-headed arrow 174 (FIGS. 12, 13A, 13B).

Separate dual-acting, air-powered linear actuators 176, 178 extend and retract a respective support 160, 162. The piston 180, 182 of respective actuator 176, 178 is connected to a respective support 160, 162 at a pivotable linkage 184, 186. At the other end of each actuator 176, 178 a linkage 188, 190 pivotally joins each actuator 176, 178 to member 158. This arrangement permits actuators 176, 178 to move laterally with respect to member 158 enabling idler rollers 164, 166 on supports 160, 162 to grip pre-filled containers 22 with three points of contact across a range of different pre-filled container 22 circumferences.

A compressed air source (not shown), tubing (not shown) and suitable valve apparatus (not shown) direct compressed air to actuators 168, 176, 178 enabling such actuators to grip a pre-filled container 22 against drive roller 150 and to release pre-filled container 22. Controller 96 enables operation of the valve apparatus and compressed air source based on a signal received via interface 108 from computer 104. Control of actuators 168, 176, 178 is well known to persons of skill in the art.

When the actuators 168, 176, 178 are in an extended position as shown in FIGS. 13B-13E and 13G, pre-filled container 22 is clamped against drive roller 150. Actuators 168, 176, 178 provide about five pounds/sq. inch of pressure to the idler rollers 164, 166. Actuators 168, 176, 178 extend member 158 and supports 160, 162 to the position shown in FIGS. 13B-13E and 13G until resistance to further extension overpowers further movement of actuators 168, 176, 178. In this manner, supports 160, 162 and idler rollers 164, 166 are self-centering to position each pre-filled container 22 against the drive roller 150 as part of the process of precisely positioning pre-filled container 22 to receive patient specific information 54, for example on label 56.

Rotation of drive roller 150 in the direction of arrow 192 causes the clamped pre-filled container 22 to rotate in an opposite direction. Rotation of clamped pre-filled container 22 may be used to scan bar code 50 to identify pre-filled container 22 to computer 104, to locate reference point 52, to rotate pre-filled container 22 to the indicia-receiving position, to apply patient-specific label 56 to pre-filled container 22 and for bar code scanning after label 56 is applied to verify to computer 104 that the correct patient-specific label 56 has been applied to pre-filled container 22.

Clamping of pre-filled container 22 against drive roller 150 by idler rollers 164, 166 of gripper 14 results in formation of a nip 194 between outer surface 25 of pre-filled container 22 and surface 154 of drive roller 150. Nip 194 is utilized to attach the patient-specific label 56 to pre-filled container 22.

Figure 13C:
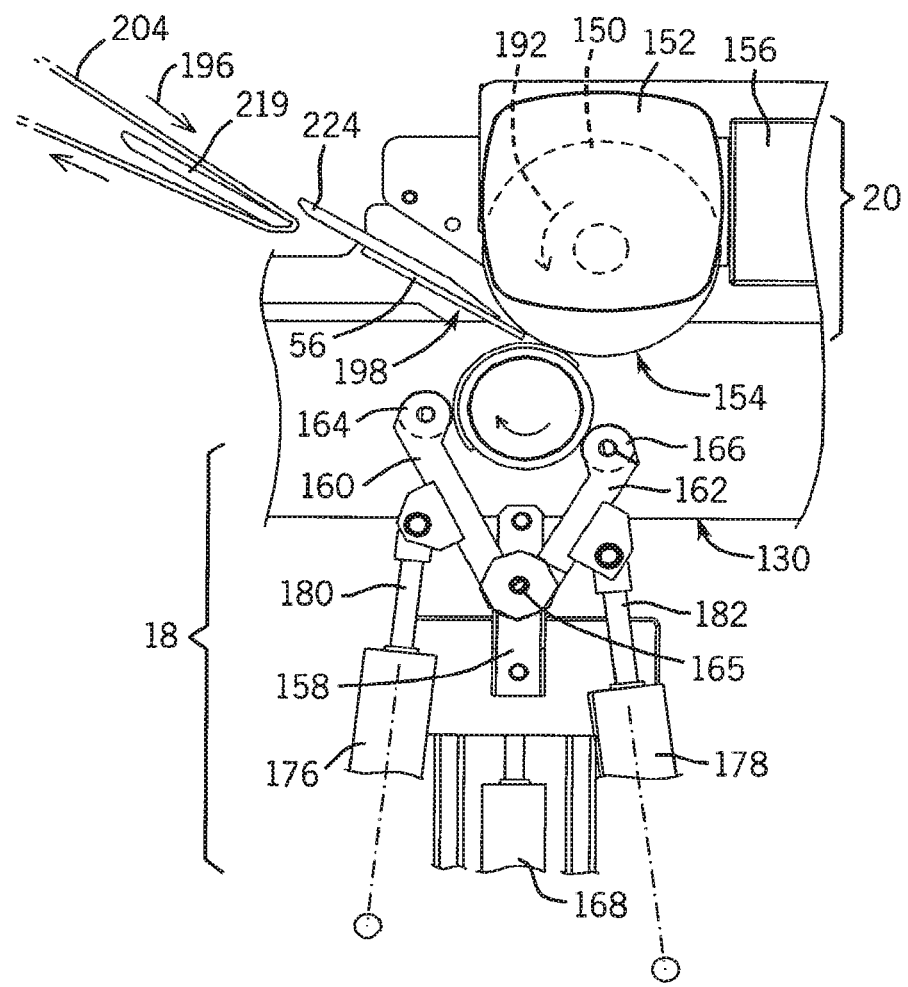
FIG. 13C is a further schematic illustration of the information-application apparatus of FIGS. 10 and 13A shown in an indicia-receiving position with the pre-filled container oriented to receive the leading edge of the label.

Pre-filled container 22 is oriented by rotation to the indicia-receiving position shown in FIG. 13C. Such position is the position enabling placement of the patient-specific information in the desired location on pre-filled container 22 as pre-filled container 22 is rotated. The indicia-receiving position will change depending on the specific location for placement of the patient-specific indicia 54 and the size and shape of pre-filled container 22.

A patient-specific label 56 is fed along a path in the direction of arrow 196 (FIGS. 13C, 13D) and into nip 194 with an adhesive-containing side 198 facing outer surface 25 of pre-filled container 22. The opposite rotation of drive roller 150 and of pre-filled container 22 at the container-receiving position (FIG. 13C) draws label 56 into nip 194 and against outer surface 25 of pre-filled container 22. Coaction of idler rollers 164, 166 of gripper 18 and drive roller 150 of drive mechanism 20 urge adhesive-containing side 198 of label 56 against pre-filled container 22 to affix label 56.

Figure 13E:
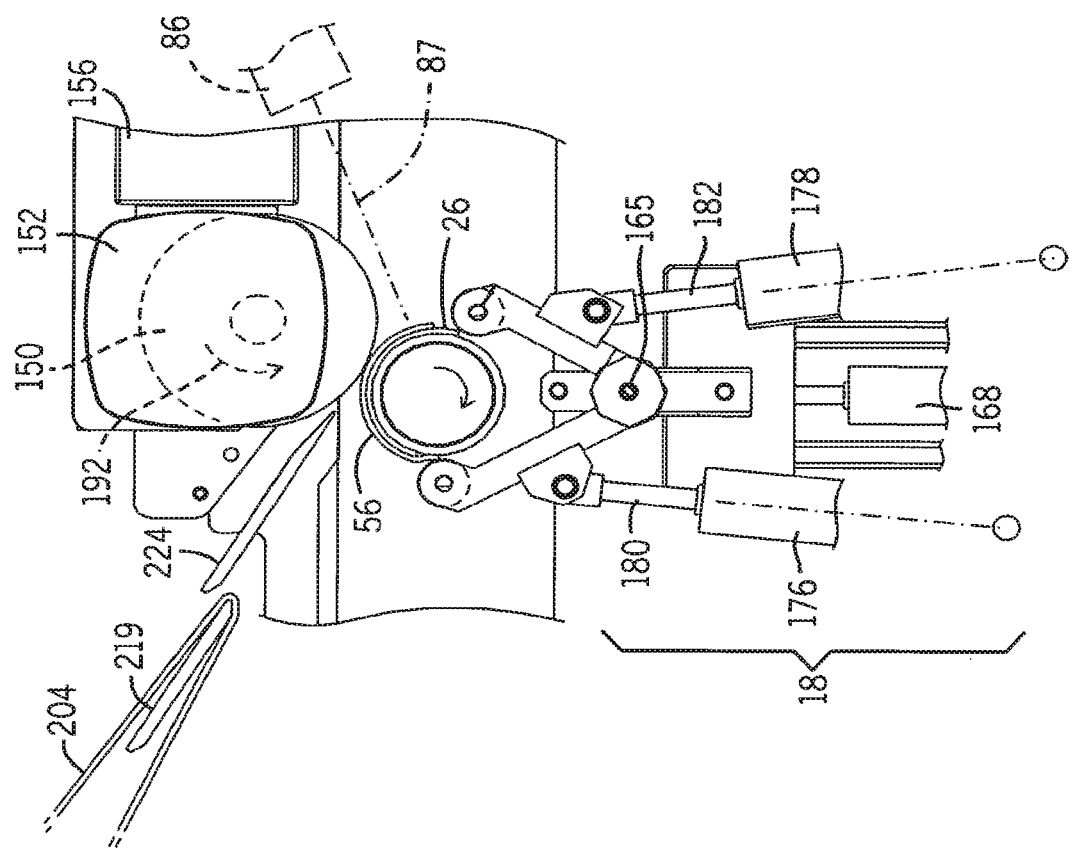
FIG. 13E is a further schematic illustration of the information-application apparatus of FIGS. 10 and 13A shown in a position verifying the pre-filled container following application of the patient-specific information and label.
Figure 13D:
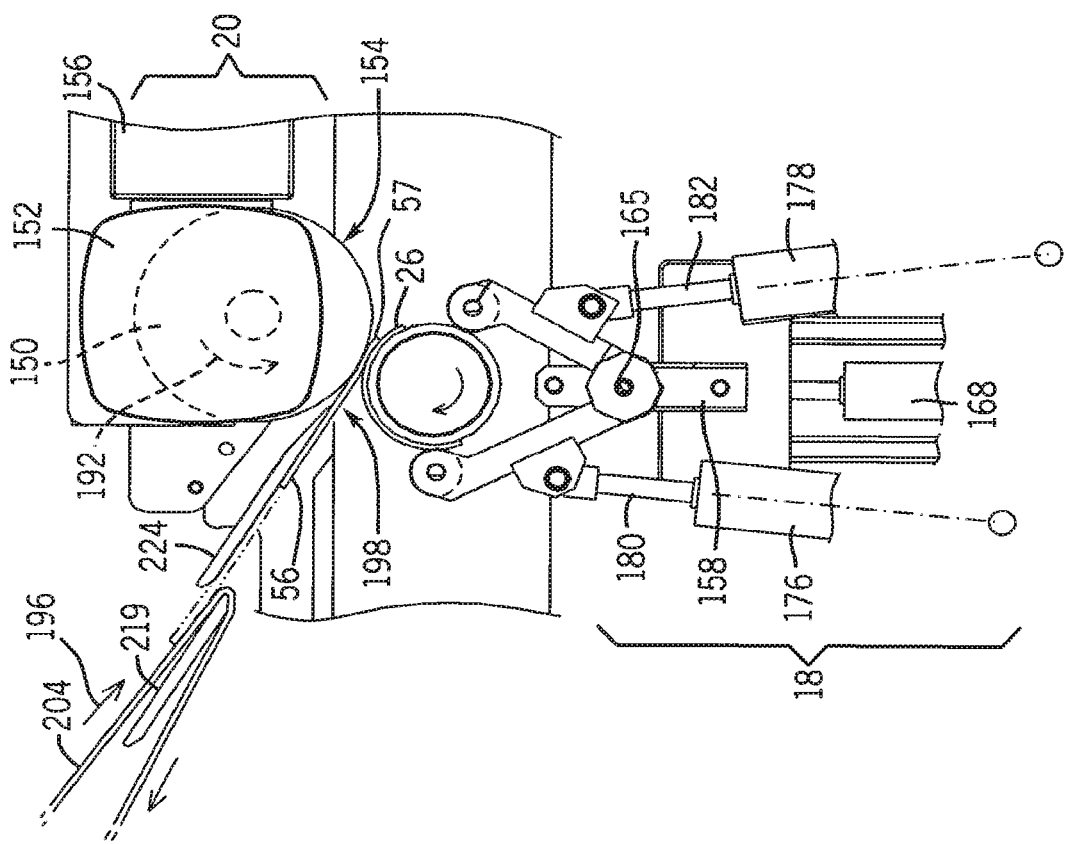
FIG. 13D is a further schematic illustration of the information-application apparatus of FIGS. 10 and 13A shown in a position receiving a precisely-positioned label with patient-specific information.
Figure 13G:
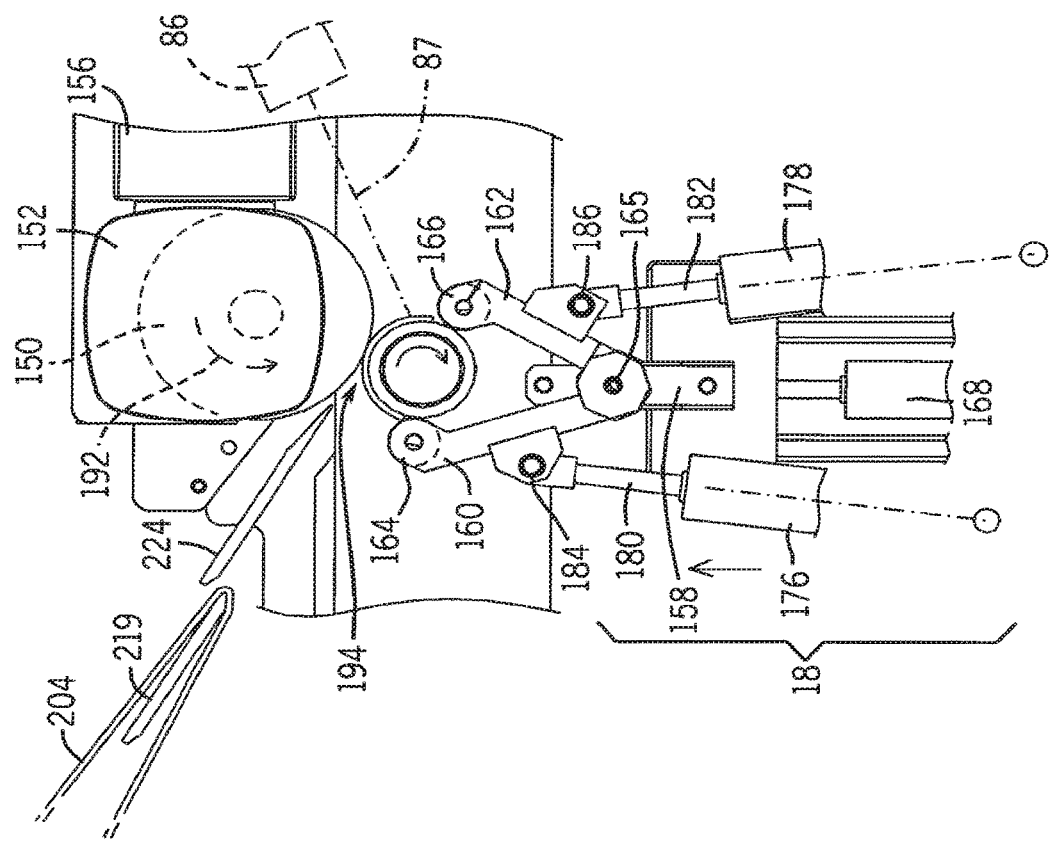
FIG. 13G is a further schematic illustration of the information-application apparatus of FIGS. 10 and 13A but with a pre-filled container of a smaller size than the pre-filled container of FIGS. 13A-13F.

As is apparent from a comparison of FIGS. 13A-13F with FIG. 13G, gripper 14 can accommodate pre-filled containers 22 of different sizes without changing a gripper or gripper part. This result is achieved by means of the extensible member 158 and supports 160, 162 which pivot at joint 165. The articulated structure of gripper 14 enables supports 160, 162 and idler rollers 164, 166 to be extended as far as necessary toward pre-filled container 22 for self-centering movement to precisely position pre-filled container 22 in position to receive label 56.

Information-application apparatus 10 further includes a reader 86 provided to identify each pre-filled container 22 to computer 104 and PPS database 106. Reader 86 may also identify the position of a gripped pre-filled container 22 so that pre-filled container 22 may be oriented for application of label 56. Reader 86 may also be used to verify that the correct patient-specific information has been applied to the pre-filled container 22. Reader 86 may comprise a single device as shown in FIGS. 9-12 or may comprise a collection of devices, each adapted to read a type of information. Reader 86 is preferably configured to scan and read bar code 50 or other machine-readable indicia affixed to pre-filled container 22 by the manufacturer or other supplier. A typical optical-type reader 86 will include a laser emitter and a detector. As represented schematically in FIGS. 13B, BE and 13G, energy beam 87 emitted from the reader 86 is reflected from bar code 50. The detector detects the pattern of reflectance and reader 86 generates a signal corresponding to code 50 which is transmitted to computer 104. Detection of bar code 50 results in generation of a signal corresponding to the unique NDC number 42 for pre-filled container 22. The signal is matched to information in the PPS database 106 on computer 104 to uniquely identify pre-filled container 22 corresponding to the bar code 50.

Reader 86 preferably detects bar code 50 as a gripped pre-filled container 22 is spun by the drive roller 150 with bar code 50 moving past reader 86. Reader 86 transmits a signal to computers 104 representative of information embedded in the bar code 50. Where an optically-detected reference point 52 is utilized, reader 86 may be further adapted to detect reference point 52 and to communicate that information to computer 104. A representative scanner is a Microscan® MS-820 industrial bar code scanner available from Microscan Systems, Inc. of Renton, Wash. Other optical systems can be used as reader 86 including camera-based systems and text-reading systems.

Reader 86 may also include apparatus to identify pre-filled containers 22 which include machine-readable information other than bar code 50 and other forms of optically-read information. For example, reader 86 may include an RFID transceiver adapted to receive information from RFID tag 51 affixed to pre-filled container 22. RFID tag 51 includes all information desired to identify pre-filled container 22 and information obtained from RFID tag 51 is transmitted to computer 104 and is used to identify pre-filled container 22 to system 80. The information may include, for example, the NDC code 42 uniquely identifying pre-filled container 22.

Once pre-filled container 22 is identified, it is matched to the corresponding prescription order. Information in database 106 is accessed and a signal sent for controller 96 via interface 108. Controller 96 interprets the signal and controls motor 152 to rotate pre-filled container 22 relative to reference point 52 and into the indicia receiving position (FIG. 13E) to receive the patient-specific information 54 for the specific patient prescription order.

Referring to FIGS. 7 and 9-13G, information application apparatus 10 further includes a printer (or print engine) 12. In the embodiment, printer 12 is adapted to generate a patient-specific label 56 for application to the pre-filled container 22. An exemplary label 56 is shown in FIGS. 3-5. Printer 12 maybe a conventional printer which preferably includes the capability of generating indica 54 including both human-readable information and machine-readable information, such as bar code 78.

Printer 12 includes a print element 200 which prints information on label 56. Print element 200 may be capable of generating indicia 54 in any suitable manner such as by direct thermal, thermal transfer, laser or ink-jet printing on label 56. A suitable label printer 12 is a Zebra® RII0 PAX 3 Print Engine available from Zebra Technologies International of Vernon Hills, Ill. As it is expected that printer technology will evolve over time, printers suitable for use as printer 12 and which are capable of affixing a wide range of information to a label 56 are expressly intended to be within the scope of the invention.

Labels 56 used in conjunction with print element 200 are preferably supplied in the form of a supply roll 202. Roll-form labels 202 are well-suited for use in a high throughput information-application apparatus 10 used in a system such as system 80.

Roll 202 includes a web 204 of release liner material (e.g., wax-coated paper) with a plurality of labels 56 spaced apart along the web 204. Labels 56 may be die cut along web to form discrete labels. Adhesive-backed side 198 of labels 56 is removably affixed to web 204 and an opposite side provided to receive information from print element 200. Labels 56 may have any suitable dimensions depending on the amount of coverage over container indicia 24 desired by pharmacy management.

As shown in FIG. 9, a feed mechanism 205 is provided to unroll web 204 from roll 202 and to supply labels 56 to print element 200 and to pre-filled container 22. In the embodiment shown, feed mechanism 205 may include any suitable apparatus for unwinding web 204 of label material from supply roll 202, feeding web 204 to print element 200 and directing printed labels 56 onto a pre-filled container 22. In the example, roll 202 is preferably powered for unwinding by one or more motors (not shown). Powered rollers 206, 208, 210, 212, 214 and 216 pull web 204 through printer 12 for take up by take-up roll reel 218.

Peel bar 219 separates labels 56 from release liner of web 204 by doubling the web back progressively separating each label 56 from the web 204 starting with the label leading edge 220 and progressively moving toward the label trailing edge 222. As label 56 is separated from web 204, skid plate 224 guides the printed surface of each label 56 toward pre-filled container 22. In the embodiment shown, printed side of label 56 faces skid plate 224 while adhesive-backed surface 198 faces away from skid plate 224 and toward a gripped pre-filled container 22 for application thereto as described in more detail below. Waste web material 204 is taken up on reel 218 and is discarded.

Application of the patient-specific indicia 54 may be verified by apparatus 10. The pre-filled container 22 is rotated until the patient-specific bar code 78 is read by reader 86 and the corresponding patient specific code signal is verified by computer 104 to a pending prescription order by reference to database 106. (FIG. 13E)

After application and verification of label 56, each pre-filled container 22 is released to conveyor 130 of transport mechanism 84. Conveyor 130 directs the pre-filled containers 22 to an apparatus 88 structured to collect and sort pre-filled containers 22 shown schematically in FIG. 7.

The collection and sortation apparatus shown schematically by reference number 88 may comprise any suitable apparatus known to persons of skill in the art for collecting the pre-filled containers 22 and grouping or sorting such containers 22 by patient prescription order. Pre-filled containers 22 for a common prescription order may be routed into a single lane, placed in a common tote, bag or other container or otherwise segregated from other pre-filled containers 22. In this way, all pre-filled containers 22 according to a single prescription order are grouped together thereby facilitating verification by a pharmacist prior to providing the pre-filled containers 22 to the patient. The OptiFill® brand robotic accumulator available from AutoMed Technologies is an example of a collecting and sorting apparatus 88 which may be employed in system 80. A collection and sortation apparatus 88 is not a requirement of system 80 as pre-filled containers 22 including patient-specific indicia 54 may be grouped manually by a pharmacy worker by other means. Articles other than pre-filled container or containers 22 may be grouped with such collected and sorted pre-filled containers 22, for example by combining pre-filled containers 22 with such further articles in a tote assigned to a particular patient prescription order.

Referring again to FIG. 7, information necessary for operation of system 80 resides on computer 104 or is accessible to computer 104. PPS software residing on computer 104 or other software controls operation of the system 80 and components 10, 82, 84, 86, 88. Controllers 94, 95, 96 and 98 interpret signals generated by computer 104 to enable operation of the specific component 10, 82, 84, 86, 88. The instructions residing on computer 104 enable operation of positioner 14 to move each pre-filled container 22 to a label-receiving position, operate printer 12 to print patient-specific indicia 54 on, for example, label 56 and operate apparatus 10 to apply indicia 54, for example on label 56, to pre-filled container 22. The instructions are described in more detail in connection with the process of operation and methods described below.

Database 106 identifying pending prescription orders and each pre-filled container 22 used in the system resides on computer 104 or is accessible to computer 104. Database 106 includes information uniquely identifying each pre-filled container 22 by means of the NDC 42 or other code detected by reader 86. Computer 104 accesses database 106 and retrieves information corresponding to the prescription order being filled and the corresponding pre-filled container 22. Pre-filled container 22 is matched to a pending patient prescription order. In addition, database 106 includes, for each pre-filled container 22, positioning information enabling positioner 14 to move each pre-filled container 22 to the proper indicia-receiving position for receiving a patient-specific label 56.

In the most highly preferred embodiments, database 106 includes information identifying each pre-filled container 22 and further identifying the time-duration of rotational displacement of pre-filled container 22 necessary to position pre-filled container 22 adjacent the skid plate 224 to receive label 56 in the desired location. This is the indicia-receiving position shown in FIG. 13C. The time duration may be determined with reference to a time duration required for pre-filled container 22 to rotate to a desired position once reference point 52 has been identified to computer 104. Computer 104 through controller 96 triggers operation of printer 12 at the appropriate time to locate label 56 leading edge 220 exactly at the desired position. The result is precise placement of the label 56 as shown in FIGS. 4, 5 and 13C-13G. Database 106 is programmed to generate the appropriate signal triggering printing based on the time duration for desired placement of indicia 54 on pre-filled container 22.

For example, a representative drive roller 150 may have a 6 inch diameter and be powered to rotate by motor 152 at 30 RPM. The circumference of roller 150 in the example is 18.84 inches and one full rotation of the drive roller 140 is equal to 18.84 inches. At 30 RPM, the drive roller 150 rotates 0.5 revolution/second. Therefore speed is 9.42 inches/second at 30 RPM (18.84 inches/rotation×0.5 rotations/second).

Table 1 sets forth the operational time for rotation of pre-filled container 22 15 following detection of reference point 52 based on the exemplary conditions set forth above.

TABLE 1

| Pre-Filled Container Example | Spacial Distance Between Position of Pre-Filled Container Relative to Reference Point and Label Leading Edge Placement (Inches) | Time Duration of Rotation (Seconds) |
| --- | --- | --- |
| 1 | 1.00 | 0.106 seconds (106 msec) |
| 2 | 3.00 | 0.318 seconds (318 msec) |
| 3 | 0.50 | 0.053 seconds (53 msec) |

For a selected pre-filled container 22, it may be desired to place the leading edge 220 of patient-specific label 56 on pre-filled container 22 one inch past the position of pre-filled container 22 when reference point 52 is identified to computer 104 or controller 96. The time duration of rotation would be 0.106 seconds and printer 12 would be triggered for operation such that the leading edge 220 is inserted into nip 1940.106 seconds after identification of reference point 52 to computer 104 or controller 96.

While label 56 and indicia 54 are shown applied to a sidewall of pre-filled container 22, it should be noted that such indicia 54 may be applied to other surfaces such as a bottom surface of pre-filled container 22.

Orientation processes other than by use of timing can be implemented. For example, positioner 14 may orient pre-filled container 22 by means of rotational displacement relative to reference point 52. And, use of a key associated with pre-filled container 22 and mating key way can be used to ensure displacement of pre-filled container 22 to the desired position so that indicia 54 are precisely applied to pre-filled container 22.

Information-application apparatus 10 may be scaled as appropriate to accommodate the requirements of a particular pharmacy. FIG. 15 shows an alternative information-application apparatus embodiment 10' mounted on an exemplary automatic pre-filled container dispenser 226. Such embodiment is intended for use in a medium volume pharmacy environment as either a stand-alone component or part of an overall WMS system 80.

FIGS. 16 and 17 show a further alternative embodiment information-application apparatus 10" in a stand-alone configuration. Such embodiment is intended for use in a low volume pharmacy environment as a stand-alone component.

Apparatus 10' and 10" share common parts and operational features with embodiment 10 and like reference numbers are used to describe like parts of apparatus 10, 10' and 10". The description of the structure and operation of apparatus 10 is incorporated herein by reference with respect to apparatus 10' and 10". Printer 12 is not shown in FIGS. 15-17 to facilitate understanding of apparatus 10' and 10".

Referring to FIG. 15, embodiment 10' includes a housing 135 (shown in a partial cutaway view) secured to dispenser 226 and a base 137 secured to housing 135. Dispenser 226 automatically dispenses a pre-filled container 22 into chute 128 through top opening 126. Chute 128 directs pre-filled container 22 to base 227 adjacent positioner 14.

Referring to FIGS. 16 and 17, embodiment 10" includes housing 135 (shown in a partial cutaway view) and a stand 228 with legs, such as leg 231. Stand 228 is not required and housing 135 could be adapted to rest on a tabletop surface (not shown). A pharmacy worker drops a pre-filled container 22 into chute 128 through top opening 126. Chute 128 directs pre-filled container 22 to base 227 adjacent positioner 14 as in embodiment 10'.

Each embodiment 10' and 10" includes a reader 86, a positioner 14 including a drive roller 150, motor 152, drive roller surface 154 and motor controller 156 as described in connection with embodiment 10. Embodiments 10' and 10" also include a gripper 18 as described in connection with embodiment 10. Gripper 18 includes gripper member 158, idler roller supports 160, 162, idler rollers 164, 166 actuators 168, 176, 178, pistons 180, 182 and linkages 184, 186, 188 and 190 as described in connection with embodiment 10. Member 158 translates on guides 170, 172 and operates to position a pre-filled container 22 to form a label-receiving nip 194 in the same manner as described in connection with embodiment 10. Embodiments 10' and 10" accommodate pre-filled containers 22 of different sizes as described in connection with embodiment 10.

Each of the information-application apparatus embodiments 10' and 10" is adapted to operate with a printer (not shown) and printer feed mechanism (not shown) of a type as printer 12 and feed mechanism 205 shown and described in connection with embodiment 10. The printer is preferably utilized to supply a label 56 for precise placement on pre-filled container 22. Feed mechanism 205 delivers a web 204 of label material from a roll to a peel bar and skid plate 224 using powered rollers and a take-up reel as with embodiment 10.

Figure 18A:
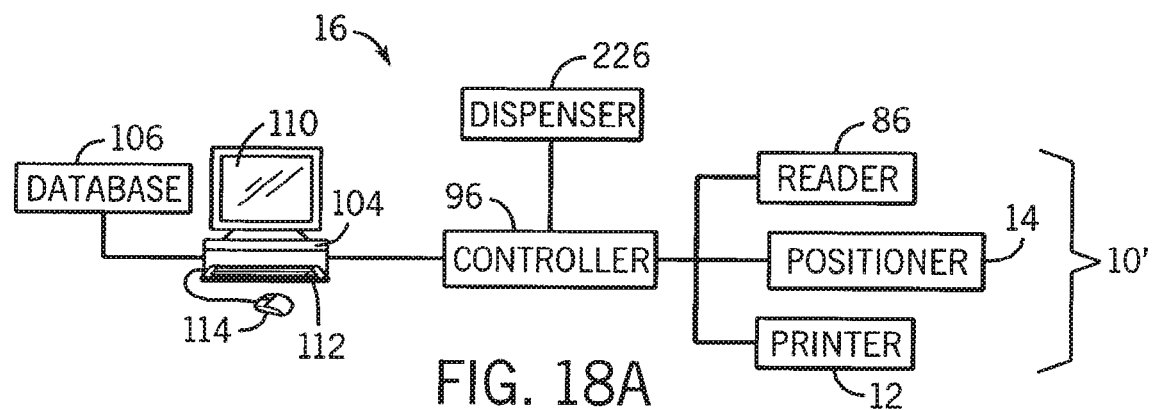
FIG. 18A is a schematic illustration showing components of an exemplary dispensing system including the information-application apparatus of FIG. 15.
Figure 18B:
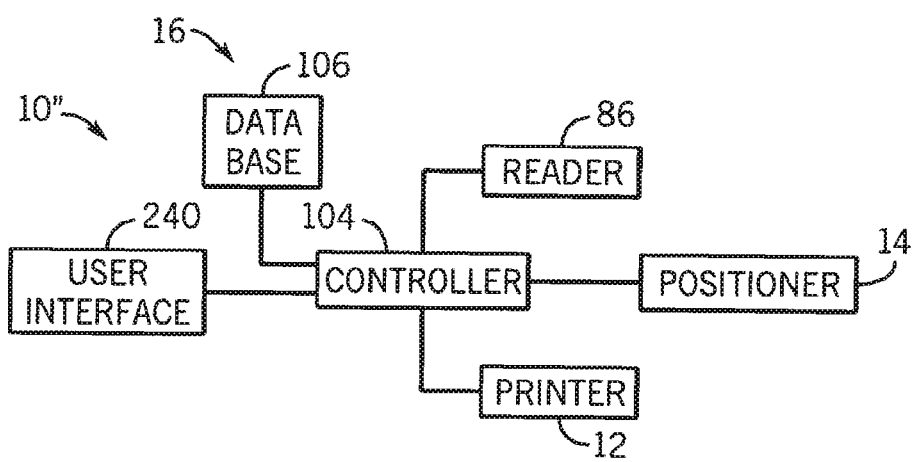
FIG. 18B is a schematic illustration showing components of an exemplary dispensing system including the information-application apparatus of FIGS. 16-17.

Referring to FIGS. 18A and 18B, each embodiment 10' and 10" is provided with control apparatus 16. Control apparatus 16 for apparatus 10' may comprise computer 104 and controller 96 (such as a PLC) as described in connection with information-application apparatus 10. Control apparatus 16 of embodiment 10" may comprise an on-board controller 104 as represented schematically in FIG. 18B. Apparatus 10' and 10" may optionally interface with a PIS 100 through any suitable means including computer 102 and 104. A database 106 residing on computer 104 enables operation of embodiments 10' and 10" to precisely apply information 54 as described in connection with embodiment 10. A user interface 240, such as a touch screen display, is provided to permit a pharmacy worker to interface with stand-alone apparatus 10".

Optionally, each of embodiments 10' and 10" is provided with an ejection mechanism in the form of a linear actuator 230. Piston (not shown) of actuator 230 extends to push a labeled pre-filled container 22 into discharge chute 234 for manual removal by a pharmacy worker.

Figure 13F:
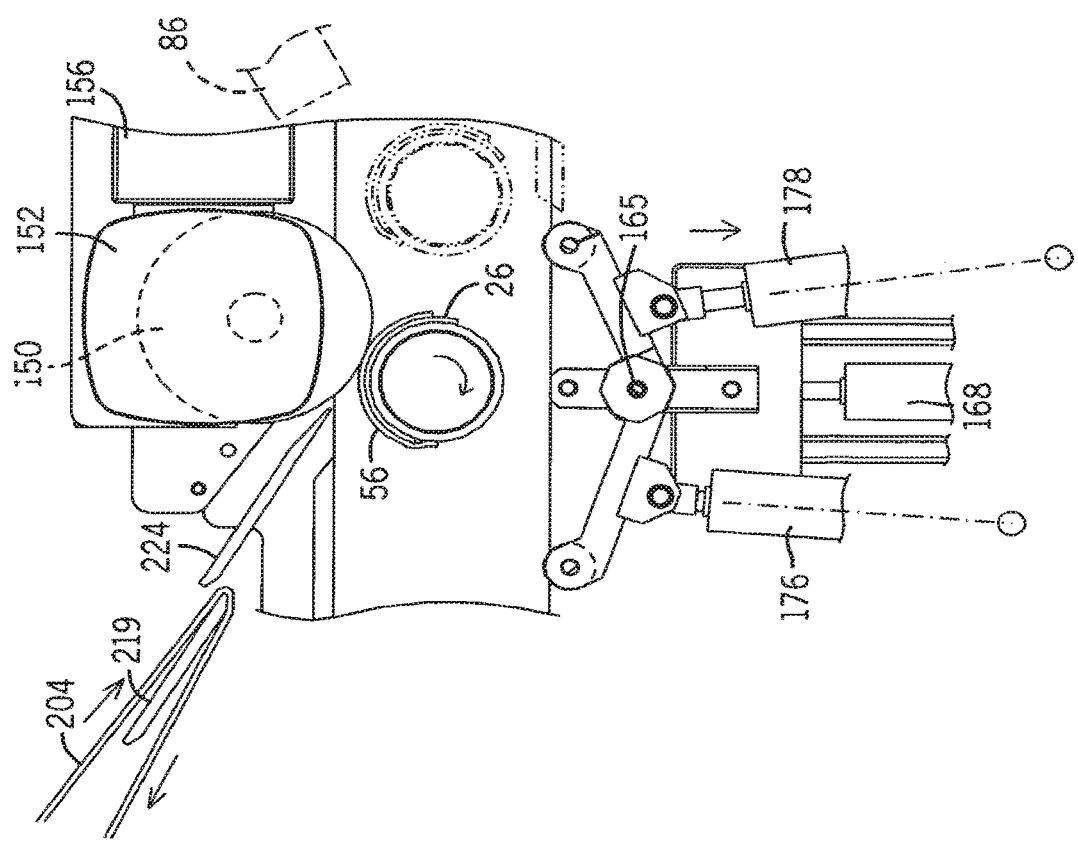
FIG. 13F is a further schematic illustration of the information-application apparatus of FIGS. 10 and 13A shown in a position releasing the pre-filled container.
Figure 14A:
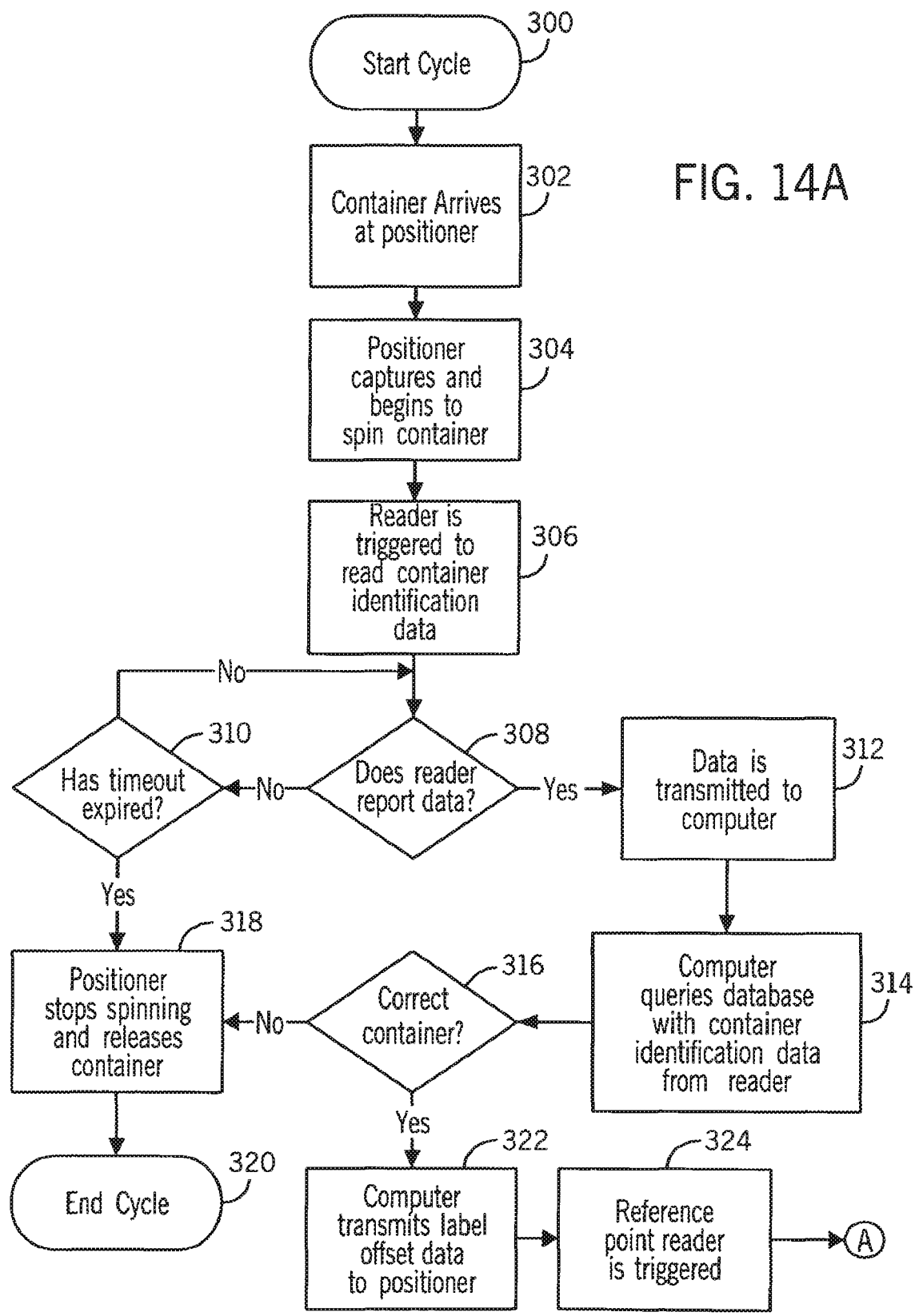
FIGS. 14A, 14B and 14C are a single logic flow diagram showing exemplary process steps for operation of an exemplary information-application apparatus.
Figure 14B:
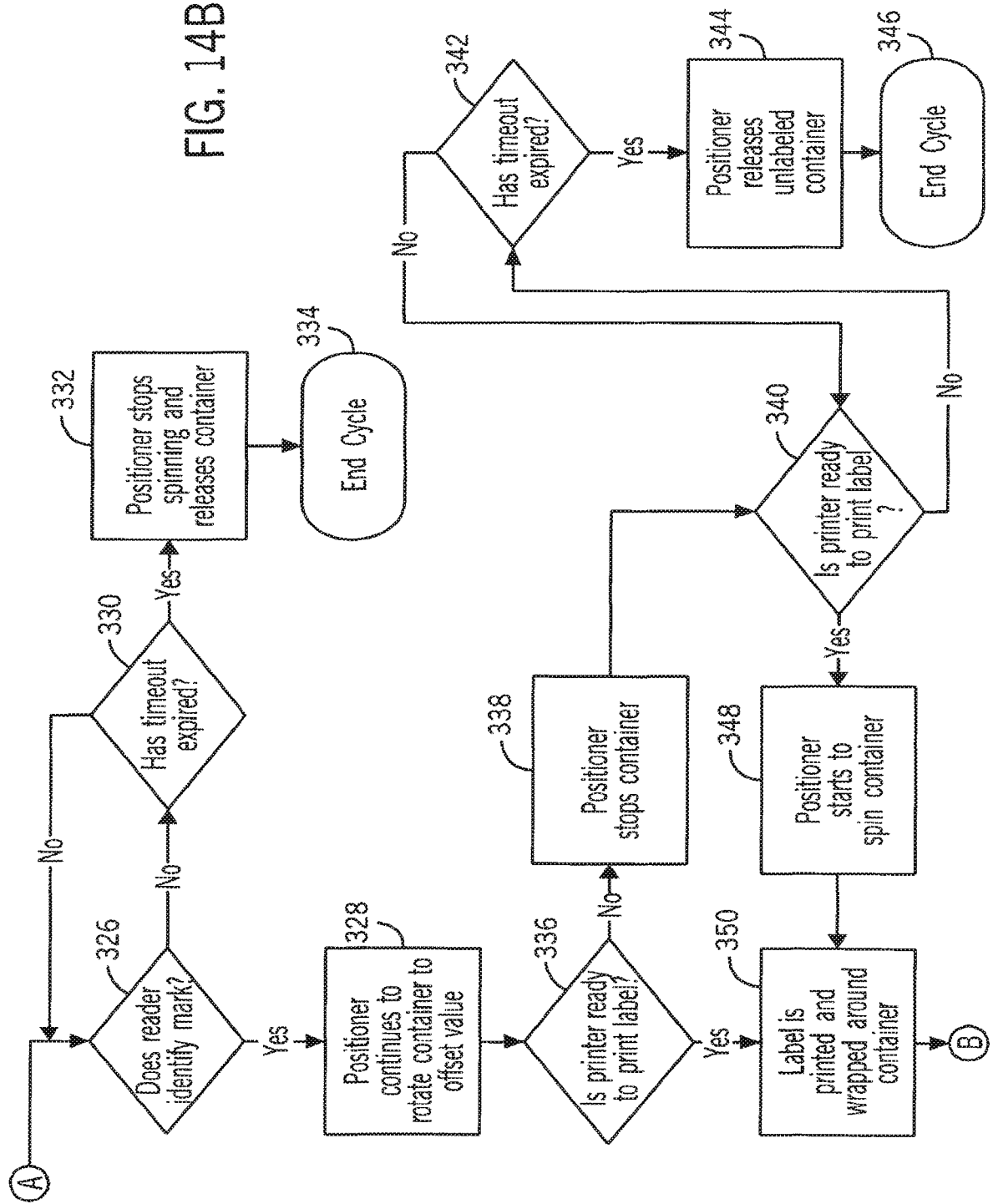
Figure 14C:
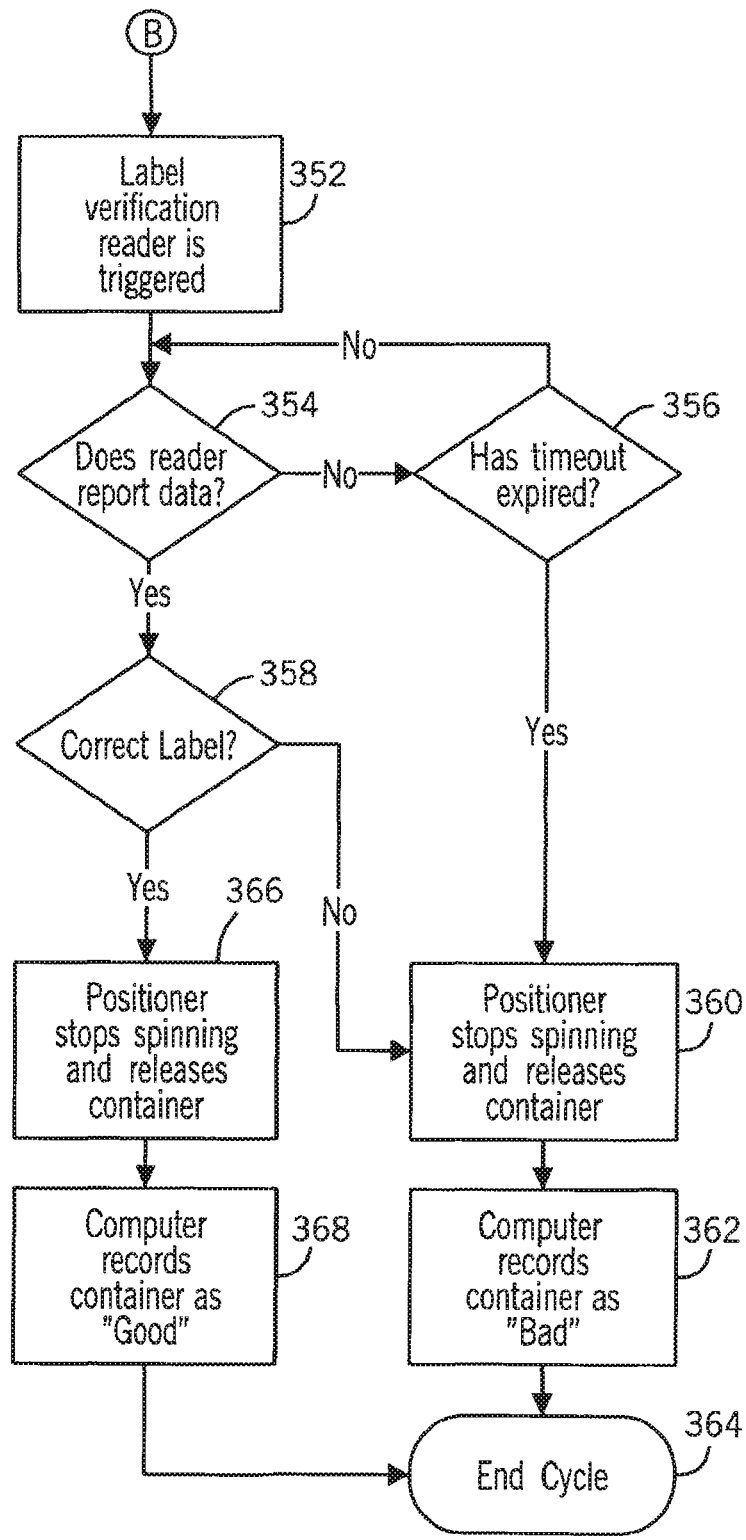

FIGS. 14A, 14B and 14C are a diagram showing the software logic flow from the point where a pre-filled container 22 arrives at positioner 14. Accordingly, such logic flow describes operation of each of apparatus 10, 10' and 10". The logic flow is described in connection with FIGS. 13A-13G which illustrate operation of a positioner 14 utilized in each of embodiments 10, 10' and 10".

As is apparent, the manner in which pre-filled container 22 arrives at positioner 14 is not critical. For automated systems, any number of different dispensers and types of container transport mechanisms 84 may be used. A dispenser (e.g., dispenser 82 or 226) and container transport mechanism 84 are not required; pre-filled container 22 may be manually selected from inventory and manually introduced to apparatus 10 as is noted with alternative embodiments 10' and 10" discussed herein.

The logic flow diagrams 14A, 14B and 14C describe operation of information-application apparatus 10, 10' and 10" adapted to precisely apply patient-specific information 54 by means of label 56. Referring then to FIG. 14A, a labeling cycle is initiated (point 300) upon delivery of pre-filled container 22 to information-application apparatus 10 as indicated in step 302. Once pre-filled container 22 is delivered to information-application apparatus 10, 10' and 10", positioner 14 will capture pre-filled container 22 and position it to receive label 56 (step 304).

Capture of pre-filled container 22 is illustrated in FIGS. 13A and 13B. Instructions residing on computer 104 and, optionally on controller 96, control operation of actuators 168, 176, 178 to manipulate gripper 18 to clamp pre-filled container 22 against drive roller 150. As shown in FIG. 13A, actuator 176 partially retracts idler roller support 162 to permit pre-filled container 22 to pass. Actuator 178 partially extends idler roller support 160 and idler roller 166 across the path of a released container 22 moving on conveyor 130 to block further movement of pre-filled container 22.

Next, and as shown in FIG. 13B, gripper member 158 is moved toward drive roller by means of actuator 168. Actuators 168, 176 and 178 further extend in a self-centering manner until rollers 164 and 166 clamp pre-filled container 22 firmly against drive roller 150. The preferred positioner 14 gripper mechanism 18 shown in FIGS. 13A-13G will automatically adjust to accommodate multiple pre-filled container 22 diameters to locate pre-filled containers 22 in the proper position to receive a patient-specific label 56.

According to step 304, positioner 14 (through motor 152 and drive roller 150) spins pre-filled container 22 clamped against drive roller 150.

In step 306, and as shown in FIG. 13B, motor 152 powers drive roller 150 to rotate counterclockwise in the direction of arrow 192. Spinning of pre-filled container 22 triggers reader 86 to read machine-readable information 50 identifying pre-filled container 22 to database 106 on computer 104. As noted elsewhere, reader 86 is configured to read bar code 50 of indicia 24 or a data storage device 51 associated with pre-filled containers 22 to identify container 22.

Reader 86 remains in operation until a determination is made (decision point 308) that the data has been read or a time out occurs at decision point 310. If the data is read, the data is transmitted to computer 104 in step 312.

In step 314, computer 104 performs a database query to determine if information-application apparatus 10, 10' and 10" has the correct pre-filled container 22 and to determine what time duration parameters to use to apply label 56. As noted elsewhere, database 106 can be a local database containing only the information required to operate information-application apparatus 10, 10' and 10" or a remote database containing information for operation of multiple areas of the pharmacy. Preferably, database 106 is integrated directly with the PPS software, reducing the amount of redundant data and communications.

In the event that pre-filled container 22 is incorrect or that a time out has occurred because the container bar code 50 cannot be read (decision point 316), positioner 14 will stop spinning pre-filled container 22 and release the un-labeled pre-filled container 22 at step 318. A reject station (not shown) will reject pre-filled container 22 into an error bin (not shown) ending the cycle (point 320).

If pre-filled container 22 is correct, computer 104 will communicate a signal representing label offset data to the controller 96 and information-application apparatus 10, 10' and 10" (step 322). Such offset data may represent a time duration between which reference point 52 is identified and when the leading edge 220 of label 56 is to be affixed to pre-filled container 22. Drive roller 150 of positioner 14 preferably will continue to rotate pre-filled container 22. Computer 104 detects the rotation and triggers reader 86 to read the position of reference point 52 on pre-filled container 22 (step 324). Reader 86 has the capability to read container reference point 52 component of indicia 24 (and a data storage device 51 if provided). Reference point 52 and bar code 50 of indicia 24 can be the same component. One embodiment of this is to use bar code 50 containing the container identification information as both the identification component and reference point 52. As illustrated in FIGS. 2 and 5, leading edge of bar code 50 could serve as reference point 52.

Referring next to FIG. 14B, once reference point 52 is identified (decision point 326), positioner 14 continues to rotate pre-filled container 22 for a time duration based on information provided by computer 104 for the specific pre-filled container 22 in process. Rotation continues until reference point 52 is in the proper position in relation to label printer 12 print element 200 (step 328). If reference point 52 is not identified within a timeout period (decision point 330), positioner 14 will stop spinning pre-filled container 22 and release the unlabeled container 22 (step 332). The reject station (not shown) will reject pre-filled container 22 into an error bin ending the cycle (point 334).

Next, a determination is made at point 336 regarding whether printer 12 is ready to print patient-specific label 56. Printer 12 may be incapable of printing due to a mechanical failure, depletion of ink or shortage of label material 204. If printer 12 is not ready to print label 56 (decision point 336), then positioner 14 stops rotating pre-filled container 22 (step 338). Printer 12 is queried again to determine whether printer 12 is capable of printing label 56 at decision point 340. The query continues until a timeout determination is made at decision point 342. If a timeout occurs, positioner 14 releases unlabeled container 22 at step 344 ending the process at point 346.

Referring again to FIG. 14B and to FIGS. 13C, 13D, if printer 12 is ready, the positioner 14 spins the pre-filled container 22 (step 348) to the proper indicia-receiving position (FIG. 13C), label 56 is printed and is fed into nip 194 by feed mechanism 205 of powered rollers 206-216 associated with printer 12. Drive roller 150 will spin pre-filled container 22 and wrap printed label 56 around pre-filled container 22 (step 350). FIG. 13D schematically illustrates a patient-specific label 56 being pulled through nip 194 with the label adhesive backed side 198 facing pre-filled container 22. FIGS. 4, 5 and 13D-13F show an example in which patient-specific label 56 is intentionally offset from the edge of the manufacturer's label 26 based on positioning information in database 106 residing on computer 104.

Referring to FIGS. 14C and 13E, once patient-specific label 56 is wrapped, a verification step 352 occurs to confirm that the correct patient-specific label 56 has been applied to pre-filled container 22. Reader 86 is triggered in step 352. FIG. 13E schematically illustrates the label verification process. Reader 86 scans bar code 78 on patient-specific label 56 as pre-filled container 22 is rotated past reader 86.

A separate reader (not shown) could be provided to read the information on patient-specific label 56 depending on the nature of that information. For example, printer 12 could imprint the label with an RFID transponder or with indicia (for example a 2D bar code) more suitable for detection with a camera. Whether reader 86 comprises one or more devices, reader 86 must have the ability to read the label verification component of indicia 54 or data storage device.

At decision point 354, a determination is made regarding whether bar code 78 on label 56 has been properly read. If bar code 78 has not been read, reader 86 continues to attempt to read bar code 78 until a timeout occurs (decision point 356). If the bar code 78 has been properly read, the label data is compared in database 106 against the expected data for a pending prescription order being fulfilled and a pass/fail determination is made (decision point 358).

If the timeout occurs or if the label 56 and bar code 78 fails the test at decision point 358, the positioner device 14 will stop spinning and release pre-filled container 22 (step 360). The computer 104 will then record the container 22 as "bad" or defective (step 362) and the cycle is ended at point 364.

If the label passes the test at decision point 358, then positioner device 14 will stop spinning and release pre-filled container 22 (step 366). In this event, computer 104 will record pre-filled container 22 as "good" at (step 368). Pre-filled container 22 will be released for fulfillment of the patient prescription order ending the labeling cycle at point 364.

FIG. 13F schematically illustrates the process wherein labeled pre-filled container 22 is released. Actuator 168, retracts member 158 and actuators 168, 170 retract a respective support 160, 162. Labeled, pre-filled stock container 22 is now free to move away from the information application apparatus 10 under the power of conveyor 130.

Optional additional verification steps not shown on FIGS. 14A-14C may be undertaken. For instance, conveyor 130 may transport labeled pre-filled container 22 to reject station (not shown) where label 56 is again read by a reader (not shown). If the information in bar code 78 matches the expected data, pre-filled container 22 is considered "good" and will travel beyond the reject station. If the information in bar code 78 does not match the expected data, or the if the data in bar code 78 was unreadable, pre-filled container 22 is considered "bad" and will be rejected into an error bin.

Referring to FIGS. 4 and 5, the output of information-application apparatus 10, 10' and 10" is a patient-specific pre-filled container 22 with information specific to the patient prescription order applied thereto. The pre-filled, non-specific stock container 22 has been converted to a patient-specific container 22 suitable for fulfillment of a patient prescription order without any requirement for special modification.

Advantageously, patient-specific label 56 is precisely positioned on pre-filled container 22 so as to optimize the value of indicia 24 provided by the manufacturer, repackager or other supplier. Referring specifically to exemplary pre-filled container 22 in FIGS. 4 and 5, it is immediately apparent that patient-specific label 56 has been precisely positioned in a way which leaves lot number 38, expiration date 40, medication name 32, strength 34, quantity 44, bar code 50 and NDC 42 accessible for use by pharmacy management and the patient. This valuable information has not been covered and rendered inaccessible as would be the case with indiscriminate placement of the patient-specific label 56 on the pre-filled container 22.

A pharmacist or other person working in the pharmacy, therefore, may be able to use both the information embodied in indicia 24 supplied with each pre-filled container 22 as well as information embodied in indicia 54 provided on patient-specific label 56 to verify the suitability of the medication for the patient. Bar code 50 supplied with pre-filled container 22 can be scanned together with the patient-specific bar code 78 to provide machine verification that the contents are suitable for the patient and are as called for by the prescription order. The ability to match pre-filled container 22 contents with patient label 56 automatically may remove the need to have a pharmacist verify the prescription order, thus creating a significant reduction in the cost associated with filling a prescription order. Also as shown in FIGS. 4 and 5, it is apparent that the patient may easily read indicia 24 supplied with pre-filled container 22. This presents a further opportunity for the patient to ensure that the correct medication or other product has been provided.

While the principles of this invention have been described in connection with specific embodiments, it should be understood clearly that these descriptions are made only by way of example and are not intended to limit the scope of the invention.

What is claimed is:

1. A system for application of patient-specific information to drug containers comprising:
    a positioner configured to adjust containers including a bar code;
    a bar code reader configured to read a bar code;
    a labeler which applies labels including patient-specific information to the containers; and
    an electronic control device operably coupled to the positioner, the bar code reader and the labeler;
    wherein the electronic control device is programmed to control the positioner to adjust the containers to a label-receiving orientation at the labeler which applies the label based at least in part on the alpha-numeric information and the bar code.

2. The system of claim 1 further comprising a database accessible by the electronic control device, the database including, for each container, positioning information utilized by the electronic control device to rotate the containers for a proper amount of time such that the adhesive label is applied without obscuring a portion of the alpha-numeric information or a portion of the bar code.

3. The system of claim 1 wherein the electronic control device is configured to determine an initial orientation of the containers based upon information read by the bar code reader.

4. The system of claim 1 wherein the positioner further comprises
    a gripper configured to engage the containers; and
    a drive mechanism operative to adjust the containers when engaged by the gripper to the label-receiving orientation.

5. The system of claim 4 wherein the drive mechanism comprises:
    a motor; and
    a drive roller operatively coupled to the motor, wherein the electronic control device is configured to control the motor to drive the drive roller.

6. The system of claim 5 wherein the gripper comprises a pair of idler rollers, the idler rollers being positionable to urge the containers against the drive roller such that rotation of the drive roller moves the containers to the label-receiving orientation.

7. The system of claim 6 wherein the labeler comprises:
    a label source;
    a print element adapted to print the patient-specific information on the labels;
    a feed mechanism adapted to supply the labels to the print element from the label source;
    a peel bar configured to remove a backing from the labels exposing an adhesive surface; and
    a guide bar configured to direct the adhesive surface of the respective labels into contact with an outer surface of the containers.

8. The system of claim 1 wherein the adhesive labels each include a leading edge and trailing edge, wherein the labeler applies the respective adhesive label to the respective container by first bringing the leading edge of the respective adhesive label into contact with the respective container and then sequentially affixing the respective adhesive label to the respective container in a direction from the leading edge to the trailing edge.

9. The system of claim 1 further comprising:
    a dispenser operatively connected to the electronic control device and adapted to store and dispense the containers; and
    a transport mechanism configured to deliver the containers from the dispenser to the positioner.

10. The system of claim 9 wherein the transport mechanism comprises a conveyor.

11. The system of claim 10 further comprising an apparatus configured to collect and sort labeled containers such that containers for a common prescription order are grouped together.

12. The system of claim 1 wherein the positioner further comprises:
    a first idler roller;
    a second idler roller;

a first actuator coupled to the first idler roller and configured to move the first idler roller independent of the second idler roller; and a second actuator coupled to the second idler roller and configured to move the second idler roller independent of the first idler roller, wherein the first and second actuators are configured to the move the first and second idler rollers, respectively, to bring the first and second idler rollers into contact with the container.

13. A system for application of patient-specific information to a drug container having a first label representative of the container contents comprising:

a positioner configured to position the container, the first label covers at least a portion of the container;

a labeler configured to print and to apply a second label including patient-specific information to the container; and a controller operably coupled to the positioner and the labeler, the controller configured to control the labeler to print patient-specific information on the second label, to control the positioner to orient the container relative to the labeler at least partially based on a location of the first label, and to control the labeler to move the second label into contact with the container.

14. The system of claim 13 further comprising a reader operatively connected to the controller, the reader configured to detect a reference point and to communicate information regarding the reference point to the controller, wherein the controller utilizes the information regarding the reference point to control the positioner to orient the container.

15. The system of claim 14 wherein the positioner is configured to rotate the container at least partially based on the information regarding the reference point.

16. The system of claim 15 wherein the reader is further configured to read container-identification information associated with the container and communicate the container-identification information to the controller, and wherein the controller is configured to identify the container based on the container-identification information.

17. The system of claim 13 wherein the second label is an adhesive label, wherein the second label includes a leading edge and trailing edge, wherein the labeler applies the second label to the container by first bringing the leading edge of the second label into contact with the container and then sequentially affixing the label to the container in a direction from the leading edge to the trailing edge.

18. The system of claim 17 wherein the controller is configured to control the labeler such that both the leading edge and the trailing edge of the second label are attached to the container after attachment of the second label such that the first label does not overlap the first label.

19. A method of adapting a stock container for use as a patient-specific container through application of a label including patient-specific information to the container comprising the steps of:

providing the stock container to a labeler in a first orientation, the container having a reference point and a first label including first indicia representative of the container contents;

determining the first orientation of the container based at least partly on the reference point;

controlling a positioner with the electronic control device to move the container from the first orientation to a label application orientation based upon the determined first orientation of the container;

printing a second label including patient specific information via a labeler; and controlling the labeler with the electronic control device to move at least one of the second label and the container into contact.

20. The method of claim 19 wherein controlling the labeler to move at least one of the second label and the container comprises bringing a leading edge of the second label into contact with the container and then affixing the second label to the container in a direction from the leading edge to a trailing edge.

* * * * *